US011845946B2

(12) United States Patent
Shen et al.

(10) Patent No.: US 11,845,946 B2
(45) Date of Patent: Dec. 19, 2023

(54) TOBACCO PLANTS EXHIBITING ALTERED PHOTOSYNTHESIS AND METHODS OF MAKING AND USING

(71) Applicant: Altria Client Services LLC, Richmond, VA (US)

(72) Inventors: Yanxin Shen, Glen Allen, VA (US); Dongmei Xu, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 34 days.

(21) Appl. No.: 17/518,303

(22) Filed: Nov. 3, 2021

(65) Prior Publication Data

US 2022/0049266 A1 Feb. 17, 2022

Related U.S. Application Data

(63) Continuation of application No. 16/579,271, filed on Sep. 23, 2019, now Pat. No. 11,174,490, which is a continuation of application No. 15/486,841, filed on Apr. 13, 2017, now Pat. No. 10,457,953.

(60) Provisional application No. 62/322,001, filed on Apr. 13, 2016.

(51) Int. Cl.
| | |
|---|---|
| *C12N 15/82* | (2006.01) |
| *C07K 14/415* | (2006.01) |
| *C12N 9/02* | (2006.01) |
| *A01H 1/06* | (2006.01) |
| *A01H 5/12* | (2018.01) |
| *A24B 13/00* | (2006.01) |

(52) U.S. Cl.
CPC ............ *C12N 15/8261* (2013.01); *A01H 1/06* (2013.01); *A01H 5/12* (2013.01); *A24B 13/00* (2013.01); *C07K 14/415* (2013.01); *C12N 9/0073* (2013.01); *C12N 15/825* (2013.01); *C12N 15/8218* (2013.01); *C12N 15/8251* (2013.01); *C12N 15/8269* (2013.01); *C12Y 114/13122* (2013.01); *Y02A 40/146* (2018.01)

(58) Field of Classification Search
CPC ............ A01H 6/823; A01H 5/12; A01H 1/06
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh et al. |
| 4,660,577 A | 4/1987 | Sensabaugh et al. |
| 4,683,195 A | 7/1987 | Mullis et al. |
| 4,683,202 A | 7/1987 | Mullis et al. |
| 4,800,159 A | 1/1989 | Mullis et al. |
| 4,848,373 A | 7/1989 | Lenkey |
| 4,965,188 A | 10/1990 | Mullis et al. |
| 5,372,149 A | 12/1994 | Roth et al. |
| 10,457,953 B2 | 10/2019 | Shen et al. |
| 2004/0118422 A1 | 7/2004 | Lundin et al. |
| 2005/0178398 A1 | 8/2005 | Breslin et al. |
| 2005/0244521 A1 | 11/2005 | Strickland et al. |
| 2006/0191548 A1 | 8/2006 | Strickland et al. |
| 2012/0024301 A1 | 2/2012 | Carroll et al. |
| 2012/0031414 A1 | 2/2012 | Atchley et al. |
| 2012/0031416 A1 | 2/2012 | Atchley et al. |
| 2014/0295448 A1 | 10/2014 | Melis et al. |

OTHER PUBLICATIONS

Yang, Y. et al. Journal of Experimental Botany, 2016, vol. 67, No. 5 pp. 1297-1310. (Year: 2016).*
Friedland, N. et al. (2019) Nature Scientific Reports, vol. 9; pp. 1-12. (Year: 2019).*
Ort, D. et al. Plant Physiology Jan. 2011, vol. 155, pp. 79-85. (Year: 2011).*
Database REFSEQ NCBI Accession No. XM_009766917.1 "Predicted signal recognition particle 43 kDa protein, chloroplastic [*Nicotiana sylvestris*]", (Oct. 21, 2014).
European Search Report dated Dec. 1, 2020 issued in European Appln. 17719469.
International Search Report dated Aug. 9, 2017, issued in Int'l Appln. PCT/US2017/027391.
Kilmyuk et al., "A Chromodomain Protein Encoded by the *Arabidopsis* CAO Gene is a Plant-Specific Component of the Chloroplast Signal Recognition Particle Pathway That is Involved in LHCP Targeting," The Plant Cell, pp. 87-99 (1999).
Lunt, "5 Things You Need to Know About PA Broadleaf Tobacco" (Aug. 15, 2018) https--www.[dot]famous-smoke[dot]com/cigaradvisor/5-things-about-pennsylvania-broadleaf-tobacco pp. 1-12.
Miller et al., "A Grade Index for Type 22 and 23 Fire-Cured Tobacco," Tobacco Intern., 192:55-57 (1990).
Ort et al., "Optimizing Antenna Size to Maximize Photosynthetic Efficiency," Plant Physiology 155(1):79-85 (Nov. 15, 2010).
Arnon, "Copper Enzymes in Isolated Chloroplasts. Polyphenoloxidase in *Beta vulgaris*," Plant Physiol., 24:1-5 (1949).
Askura et al., "Non-Identical Contributions of two Membrane-Bound cpSRP Components, cpFtsY and Alb3, to thylakoid Biogenesis," The Plant Journal 56(6):1007-1017 (2008).
Chenna et al., "Multiple Sequence Alignment with the Clustal Series of Programs," *Nucleic Acids Res.*, 31(13):3497-3500 (2003).
Dayhoff et al., Chapter 22: "A Model of Evolutionary Change in Proteins," *Atlas of Protein Sequence and Structure* (Suppl. 3):345-352 (1978).
Henning et al., "The Chloroplast Signal Recognition Particle (CpSRP) Pathway as a Tool to Minimize Chlorophyll Antenna Size and Maximize Photosynthetic Productivity," *Biotechnology Advances*, 32(1):66-72 (2014).
Horsch et al., "A Simple and General Method for Transferring Genes into Plants," *Science*, 227:1229-1223 (1985).
Kirst et al., "Assembly of the Light-Harvesting Chlorophyll Antenna in the Green Alga *Chlamdomans reinhartii* Requires Expression of the TLA2-CpFTSY Gene," *Plant Physiology*,158(2):930-945 (2012).

(Continued)

*Primary Examiner* — Russell Kallis
(74) *Attorney, Agent, or Firm* — Arnold & Porter Kaye Scholer LLP

(57) ABSTRACT

This disclosure provides tobacco plants that exhibit altered photosynthesis as well as methods of making and using such plants.

20 Claims, 10 Drawing Sheets

Specification includes a Sequence Listing.

(56) References Cited

OTHER PUBLICATIONS

Kirst et al., "Truncated Photosystem Chlorophyll Antenna Size in the Green Microalga *Chlamydomonas reinhardtii* upon Deletion of the TLA3-CpSRP43 Gene," *Plant Physiol.*, 160:2251-2260 (2012).
Kirst et al., "Assembly of the Light-Harvesting Chlorophyll Antenna in the Green Alga *Chlamydomonas reinhardtii* Requires Expression of the *TLA2-CpFTSY* Gene," *Planta*, 245:1009-1020 (2017).
Kugelmann et al., "Phenotypes of Alb3p and Carotenoid Synthesis Mutants Show Similarities Regarding Light Sensitivity, Thylakoid Structure and protein Stability," *Photosynthetica*, 51(1):45-54 (2013).
Li et al., "Modularly Assembled Designer TAL Effector Nucleases for Targeted Gene Knockout and Gene Replacement in Eukaryotes," *Nucleic Acids Res.* 39(14):6315-6325 (2011).
Lichtenthaler, "Chlorophylls and Carotenoids: Pigments of Photosynthetic Biomembranes," *Methods Enzymol.*, 148:350-82 (1987).
Mayo et al., "Genetic Transformation of Tobacco NT1 Cells with *Agrobacterium Tumefaciens,*" *Nat Protoc.*, 1(3):1105-1111 (2006).
Melis et al., "Stoichiometry of System I and System II Reaction Centers and of Plastoquinone in Different photosythetic membranes," *Proc Natl. Acad. Sci. U.S.A.*, 77(8):4712-6 (1980).
Melis et al., "Mew Vistas in Measurements of Photosynthesis—Spectroscopic Methods in Photosynthesis: Photosystem Stoichiometry and Chlorophyll Antenna Size," *Philos. Trans. R. Soc. Lond. B.*, 323:397-409 (1989).
Miller et al., "A Grade Index for Type 22 and 23 Fire-Cured Tobacco," *Tobacco Science*, 56:102-104 (1990).
Okabe et al., "Genetic Characterization and High Efficiency Photosynthesis of an Aurea Mutant of Tobacco," *Plant Physiol.*, 60:15-158 (1977).
Polle et al., "tla1, a DNA Insertional Transformant of the Green Alga *Chlamydomonas reinhardtii* with a Truncated Light-Harvesting Chlorophyll Antenna Size," *Planta*, 217:49-59 (2003).
Smith et al., "Total Silencing by Intron-Spliced Hairpin RNAs," *Nature*, 407:319-20 (2000).
Wesley et al., "Construct design for Efficient, Effective and High-Throughput Gene Silencing in Plants," *The Plant J.*, 27:581-90 (2001).
Wright et al., "High-Frequency Homologous Recombination in Plants Mediated by Zinc-Finger Nucleases," *The Plant J.*, 44:693-705 (2005).
Yang et al., "*PGL*, Encoding Chlorophyllide a Oxygenase 1, Impacts Leaf Senescence and Indirectly Affects Grain Yield and Quality in Rice," *Journal of Experimental Botany*, 2016, 67(5):1297-1310 (2016).
Yoo et al., "*Arabidopis* Mesophyll Protoplasts: A Versatile Cell System for Transient Gene Expression Analysis," *Nature Protocols*, 2(7):1565-72 (2007).
Agrawal et al. "RNA Interference: Biology, Mechanism, and Applications." *Microbiology and Molecular Biology Reviews* vol. 67, No. 4, pp. 657-685 (Dec. 2003) (Washington, DC) available online DOI: 10.1128/MMBR.67.4.657-685.2003.
"Draft for Diplomatic Conference for The Revision of The International Convention for The Protection of New Varieties of Plants," Mar. 4-19, 1991 (Geneva, Switzerland).
Melis et al., "The relative absorption cross-sections of Photosystem I and Photosystem II in chloroplasts from three types of Nicotiana tabacum," *Biochim. Biophys. Acta (BBA)—Bioenergetics*, vol. 589, No. 2, pp. 275-286 (Feb. 1980) available online DOI: 10.1016/0005-2728(80)90044-4.
Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).

\* cited by examiner

SEQUENCE LISTING

```
<160> NUMBER OF SEQ ID NOS: 56

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggcttctc tattatcttc tcgtc                                          25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcatgggaag atagcattaa caaa                                           24

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atggcttctc tattatcttc tcgtctcc                                       28

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttaaatagaa tctgccacat aaatg                                          25

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 5
atggatgctc tcttcgtcaa ttcctc                                          26

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcccttgttc aacttactac att                                             23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggatgctc tgttcgtcaa ttcct                                           25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcaacttact acattctgtt gaccc                                           25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggaagcca ctgcttcttt ctcctca                                         27

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttagttcttg gccccaaaac cacgag                                          26

<210> SEQ ID NO 11
<211> LENGTH: 1116
<212> TYPE: DNA
<213> ORGANISM: Nicotiana tabacum

<400> SEQUENCE: 11

```
atggcttctc tattatcttc tcgtctccca cgtcatcttt cctctaataa accggtactc      60
ccaccatcaa gctccggttc aaatctcctt cacaacttca catataaaac ccggttcgat     120
caatcccggt tcaaatgctc agctggtgga acggggttct tcacgaagtt gggtcgtttg     180
ctgaaagaga aagcaaagag cgacgtggag aaactgttct caggattctc aaaaactcga     240
gacaatttag cagttataga tgaactcctc ctttactgga acctttctga cactgaccgt     300
gttcttgatg aacttgaaga ggttctgttg gtgtctgatt ttggcccgaa gattaccata     360
aagattgtgg agagcttgcg ggaggatata tatgggggga aaatcaaatc aggaagtgag     420
attaaaagtg ctcttaagaa gagtatcttg gatctattga ctagcaaggc acctaaaaca     480
gagctccgtc tgggcttcag gaaaccatct gtgatcatga ttgtgggcgt caacggaggt     540
gggaagacaa catctcttgg aaagctggca aatagattga agaaagaagg ggctaagata     600
ctattagcag ctggtgatac atttagagca gctgctagtg atcagttaga aatttgggct     660
gaaaggactg ttgtgagat cgttgttgct gaaaaagaga aagctaaggc atcatcagtt     720
ctttcgcagg ctgttaaaag aggaaaggaa gagggtttcg atattgtttt atgcgacaca     780
tctggccgtc tgcacaccta ctatagcttg atggaggaat tggtggcatg caaaaaagtt     840
gtcagtaaaa ttgttactgg tgcacctaat gaaatcttgc ttgtactgga tggaactact     900
ggtttaaata tgcttccaca agcaagagag tttaacgatg ttgttggagt cactggctta     960
atattgacta aacttgatgg ttctgctcga ggtggctgtg tggttagtgt ggttgatgaa    1020
cttggcattc ctgtaaagtt tgtaggtgtt ggggaaggtg tagatgacct ccaaccgttc    1080
aatgctgagg aatttgttaa tgctatcttc ccatga                              1116
```

<210> SEQ ID NO 12
<211> LENGTH: 371
<212> TYPE: PRT
<213> ORGANISM: Nicotiana tabacum

<400> SEQUENCE: 12

```
Met Ala Ser Leu Leu Ser Ser Arg Leu Pro Arg His Leu Ser Ser Asn
1               5                   10                  15

Lys Pro Val Leu Pro Ser Ser Gly Ser Asn Leu Leu His Asn
            20                  25                  30

Phe Thr Tyr Lys Thr Arg Phe Asp Gln Ser Arg Phe Lys Cys Ser Ala
        35                  40                  45

Gly Gly Thr Gly Phe Phe Thr Lys Leu Gly Arg Leu Leu Lys Glu Lys
    50                  55                  60

Ala Lys Ser Asp Val Glu Lys Leu Phe Ser Gly Phe Ser Lys Thr Arg
65                  70                  75                  80

Asp Asn Leu Ala Val Ile Asp Glu Leu Leu Tyr Trp Asn Leu Ser
                85                  90                  95

Asp Thr Asp Arg Val Leu Asp Glu Leu Glu Glu Val Leu Leu Val Ser
            100                 105                 110

Asp Phe Gly Pro Lys Ile Thr Ile Lys Ile Val Glu Ser Leu Arg Glu
        115                 120                 125

Asp Ile Tyr Gly Gly Lys Ile Lys Ser Gly Ser Glu Ile Lys Ser Ala
    130                 135                 140

Leu Lys Lys Ser Ile Leu Asp Leu Leu Thr Ser Lys Ala Pro Lys Thr
145                 150                 155                 160

Glu Leu Arg Leu Gly Phe Arg Lys Pro Ser Val Ile Met Ile Val Gly
                165                 170                 175
```

```
Val Asn Gly Gly Gly Lys Thr Thr Ser Leu Gly Lys Leu Ala Asn Arg
            180                 185                 190

Leu Lys Lys Glu Gly Ala Lys Ile Leu Leu Ala Ala Gly Asp Thr Phe
        195                 200                 205

Arg Ala Ala Ser Asp Gln Leu Glu Ile Trp Ala Glu Arg Thr Gly
    210                 215                 220

Cys Glu Ile Val Val Ala Glu Lys Lys Ala Lys Ala Ser Ser Val
225                 230                 235                 240

Leu Ser Gln Ala Val Lys Arg Gly Lys Glu Glu Gly Phe Asp Ile Val
                245                 250                 255

Leu Cys Asp Thr Ser Gly Arg Leu His Thr Tyr Tyr Ser Leu Met Glu
            260                 265                 270

Glu Leu Val Ala Cys Lys Lys Val Val Ser Lys Ile Val Thr Gly Ala
        275                 280                 285

Pro Asn Glu Ile Leu Leu Val Leu Asp Gly Thr Thr Gly Leu Asn Met
    290                 295                 300

Leu Pro Gln Ala Arg Glu Phe Asn Asp Val Val Gly Val Thr Gly Leu
305                 310                 315                 320

Ile Leu Thr Lys Leu Asp Gly Ser Ala Arg Gly Gly Cys Val Val Ser
                325                 330                 335

Val Val Asp Glu Leu Gly Ile Pro Val Lys Phe Val Gly Val Gly Glu
            340                 345                 350

Gly Val Asp Asp Leu Gln Pro Phe Asn Ala Glu Glu Phe Val Asn Ala
        355                 360                 365

Ile Phe Pro
    370

<210> SEQ ID NO 13
<211> LENGTH: 966
<212> TYPE: DNA
<213> ORGANISM: Nicotiana tabacum

<400> SEQUENCE: 13
atggcttctc tattatcttc tcgtctccca catcatcttt cctctaataa accggtactc      60
ccaccatcaa gctccggttc aaatctcctt cacaacttca catataaaac ccggttcgat     120
caatcccggt tcaaatgctc agctggtgga acggggttct tcacgaagtt gggtcgtttg     180
ctgaaagaga aagcaaagag cgacgtggag aaactgttct caggattctc aaaaactcga     240
gacaatttag cagttataga tgaactcctc ctttactgga acctttctga cactgaccgt     300
gttcttgatg aacttgaaga ggttctgttg gtgtctgatt ttggcccgaa gattaccata     360
aagattgtgg agagcttgcg ggaggatata tatgggggga aaatcaaatc aggaagtgag     420
attaaaagtg ctcttaagaa gagtatcttg gatctattga ctagcaaggc acctaaaaca     480
gagctccgtc tgggcttcag gaaaccatct gtgatcatga ttgtgggcgt caacggaggt     540
gggaagacaa catctcttgg aaagctggca aatagattga agaagaaggg gctaagata      600 ctattagcag ctggtgatac atttagagca gctgctagtg atcagttaga aatttgggct     660
gaaaggactg gttgtgagat cgttgttgct gaaaaagaga agctaaggc atcatcagtt      720 ctttcgcagg ctgttaaaag aggaaaggaa gagggttttcg atattgtttt atgcgacaca     780
tctggccgtc tgcacaccta ctatagcttg atggaggaat tggtggcatg caaaaaagtt     840
gtcagtaaaa ttgttactgg tgcacctaat aggagcagta tacaacagga actaagatta     900
gcagcttgct actactctga aaattcaaca ttcacaaata catttatgt ggcagattct      960
``` atttaa																	966

<210> SEQ ID NO 14
<211> LENGTH: 320
<212> TYPE: PRT
<213> ORGANISM: Nicotiana tabacum

<400> SEQUENCE: 14

Met Ala Ser Leu Leu Ser Ser Arg Leu Pro His His Leu Ser Ser Asn
1               5                   10                  15

Lys Pro Val Leu Pro Ser Ser Gly Ser Asn Leu Leu His Asn
            20                  25                  30

Phe Thr Tyr Lys Thr Arg Phe Asp Gln Ser Arg Phe Lys Cys Ser Ala
            35                  40                  45

Gly Gly Thr Gly Phe Phe Thr Lys Leu Gly Arg Leu Leu Lys Glu Lys
        50                  55                  60

Ala Lys Ser Asp Val Glu Lys Leu Phe Ser Gly Phe Ser Lys Thr Arg
65                  70                  75                  80

Asp Asn Leu Ala Val Ile Asp Glu Leu Leu Leu Tyr Trp Asn Leu Ser
                85                  90                  95

Asp Thr Asp Arg Val Leu Asp Glu Leu Glu Glu Val Leu Leu Val Ser
            100                 105                 110

Asp Phe Gly Pro Lys Ile Thr Ile Lys Ile Val Glu Ser Leu Arg Glu
        115                 120                 125

Asp Ile Tyr Gly Gly Lys Ile Lys Ser Gly Ser Glu Ile Lys Ser Ala
    130                 135                 140

Leu Lys Lys Ser Ile Leu Asp Leu Leu Thr Ser Lys Ala Pro Lys Thr
145                 150                 155                 160

Glu Leu Arg Leu Gly Phe Arg Lys Pro Ser Val Ile Met Ile Val Gly
                165                 170                 175

Val Asn Gly Gly Gly Lys Thr Thr Ser Leu Gly Lys Leu Ala Asn Arg
            180                 185                 190

Leu Lys Lys Glu Gly Ala Lys Ile Leu Leu Ala Ala Gly Asp Thr Phe
        195                 200                 205

Arg Ala Ala Ala Ser Asp Gln Leu Glu Ile Trp Ala Glu Arg Thr Gly
    210                 215                 220

Cys Glu Ile Val Val Ala Glu Lys Glu Lys Ala Lys Ala Ser Ser Val
225                 230                 235                 240

Leu Ser Gln Ala Val Lys Arg Gly Lys Glu Gly Phe Asp Ile Val
                245                 250                 255

Leu Cys Asp Thr Ser Gly Arg Leu His Thr Tyr Tyr Ser Leu Met Glu
            260                 265                 270

Glu Leu Val Ala Cys Lys Lys Val Val Ser Lys Ile Val Thr Gly Ala
        275                 280                 285

Pro Asn Arg Ser Ser Ile Gln Gln Glu Leu Arg Leu Ala Ala Cys Tyr
    290                 295                 300

Tyr Ser Glu Asn Ser Thr Phe Thr Asn Asn Ile Tyr Val Ala Asp Ser
305                 310                 315                 320

<210> SEQ ID NO 15
<211> LENGTH: 1121
<212> TYPE: DNA
<213> ORGANISM: Nicotiana tabacum

<400> SEQUENCE: 15
atggatgctc tcttcgtcaa ttcctctctc tcccgcctca aactcaaatt ctcccctcaa     60

```
ttccctccca ccttctctca tcaacctttt atctgtctaa agaaactcgg caataagaac    120
aatttatcag tatttgctac gcttcagaac cagcagcaac aagcagtcga agcagcagaa    180
gacgaagaac cggtactgtt tgaagattac gatgaggatg aaacgtacgg agaagttaac    240
aaaattatcg gcagtcgagc aattgaacgt gggaaaggaa tggagtactt gatagagtgg    300
aaagacgaac atgccccaac gtgggtcccc tctgattaca ttgctaaaga tgttgtggcc    360
gagtacgaaa ctccttggtg gaatgcggct aaaaaggccg acgaatccgc tcttagggaa    420
ctcctagaaa ctgacgacga cagagatgtg gacgcagtag atgaggatgg acgtacggct    480
ttgctctttg tctcgggtct ggggtccgag ccgtgtgtca agctgctagc tgaagccggc    540
gctgacgtgg actatcgcga taggaatggc ggcttgactg ctctgcatat ggcagccggc    600
tatgttaagc cgggtgtcgc caagctgtta attgacctcg gggcagaccc cgaggtcgag    660
gattatagag gacaaacgcc tctgagcttg gcgaggatga ttttgaatca aacgcctaaa    720
ggaaatccaa tgcaattcgc gaggagattg gggttagaga atgtggttag gattttggag    780
gatgcgattt tcgagtatgc aacagtggag gaaatattgg agaagagagg gaaaggcgaa    840
aatgtggagt atttagtgaa gtggaaggat ggggaggata cgagtgggt caaagcatgg     900 ctgatatctg aagatttggt gagggatttt gaggctggtt tggaatatgc agtagcagat    960
tgtattcttg agaagagaga aggtgaggat gggaagggag aatacttggt taaatggact   1020
gatattgagg aagctacgtg ggaacccgaa gaaaatgttg accccttct tatagaagat   1080 tttgaaaaga gtcaacagaa tgtagtaagt tgaacaaggg c                       1121
```

<210> SEQ ID NO 16
<211> LENGTH: 370
<212> TYPE: PRT
<213> ORGANISM: Nicotiana tabacum

<400> SEQUENCE: 16

```
Met Asp Ala Leu Phe Val Asn Ser Ser Leu Ser Arg Leu Lys Leu Lys
1               5                   10                  15

Phe Ser Pro Gln Phe Pro Pro Thr Phe Ser His Gln Pro Phe Ile Cys
            20                  25                  30

Leu Lys Lys Leu Gly Asn Lys Asn Asn Leu Ser Val Phe Ala Thr Leu
        35                  40                  45

Gln Asn Gln Gln Gln Gln Ala Val Glu Ala Ala Glu Asp Glu Glu Pro
    50                  55                  60

Val Leu Phe Glu Asp Tyr Asp Glu Asp Glu Thr Tyr Gly Glu Val Asn
65                  70                  75                  80

Lys Ile Ile Gly Ser Arg Ala Ile Glu Arg Gly Lys Gly Met Glu Tyr
                85                  90                  95

Leu Ile Glu Trp Lys Asp Glu His Ala Pro Thr Trp Val Pro Ser Asp
            100                 105                 110

Tyr Ile Ala Lys Asp Val Val Ala Glu Tyr Glu Thr Pro Trp Trp Asn
        115                 120                 125

Ala Ala Lys Lys Ala Asp Glu Ser Ala Leu Arg Glu Leu Leu Glu Thr
    130                 135                 140

Asp Asp Asp Arg Asp Val Asp Ala Val Asp Glu Asp Gly Arg Thr Ala
145                 150                 155                 160

Leu Leu Phe Val Ser Gly Leu Gly Ser Glu Pro Cys Val Lys Leu Leu
                165                 170                 175

Ala Glu Ala Gly Ala Asp Val Asp Tyr Arg Asp Arg Asn Gly Gly Leu
```

```
            180                 185                 190
Thr Ala Leu His Met Ala Ala Gly Tyr Val Lys Pro Gly Val Ala Lys
            195                 200                 205
Leu Leu Ile Asp Leu Gly Ala Asp Pro Glu Val Glu Asp Tyr Arg Gly
            210                 215                 220
Gln Thr Pro Leu Ser Leu Ala Arg Met Ile Leu Asn Gln Thr Pro Lys
225                 230                 235                 240
Gly Asn Pro Met Gln Phe Ala Arg Arg Leu Gly Leu Glu Asn Val Val
                    245                 250                 255
Arg Ile Leu Glu Asp Ala Ile Phe Glu Tyr Ala Thr Val Glu Glu Ile
                260                 265                 270
Leu Glu Lys Arg Gly Lys Gly Glu Asn Val Glu Tyr Leu Val Lys Trp
            275                 280                 285
Lys Asp Gly Glu Asp Asn Glu Trp Val Lys Ala Trp Leu Ile Ser Glu
        290                 295                 300
Asp Leu Val Arg Asp Phe Glu Ala Gly Leu Glu Tyr Ala Val Ala Asp
305                 310                 315                 320
Cys Ile Leu Glu Lys Arg Glu Gly Glu Asp Gly Lys Gly Glu Tyr Leu
                    325                 330                 335
Val Lys Trp Thr Asp Ile Glu Glu Ala Thr Trp Glu Pro Glu Glu Asn
                340                 345                 350
Val Asp Pro Leu Leu Ile Glu Asp Phe Glu Lys Ser Gln Gln Asn Val
            355                 360                 365
Val Ser
    370

<210> SEQ ID NO 17
<211> LENGTH: 1113
<212> TYPE: DNA
<213> ORGANISM: Nicotiana tabacum

<400> SEQUENCE: 17
atggatgctc tgttcgtcaa ttcctctctc tcccgcctca aactcaaatt ctcccctcaa      60
ttccctccca ccttctctca tcaacctttt atccgtctaa agaaactcgg caacaagaac     120
aatttctcag tatttgctac gcttcagaac cagcagcaac aagcagtcgc agctgctgaa     180
gaggaagaac cggtactgtt tgaagattac gatgaggatg aaacgtacgg agaagttaac     240
aaaatcatcg gaagtagagc aattgaaggt gggaaaggaa tggagtactt gatagagtgg     300
aaagacgaac atgccccaac atgggtcccc tctgattaca ttgctaaaga tgttgtggcc     360
gagtacgaaa ctccttggtg gaatgccgct aaaaaggccg acgaatccgc tcttaagaaa     420
tttctagaag ctgacgacga cagagatgtg gacgcagttg atgaggatgg acgtacggct     480
tgctctcttg tctcgggtct ggggtccgag ccgtgtgtca agctgctagc tgaagctggc     540
gctgacgtgg actatcgcga taggaatggc ggcttgacgg ctctgcacat ggcagccggc     600
tatgttaagc cgggtgtcgc caagctgtta attgacctcg gggcagaccc tgaggtcgag     660
gattatagag acaaacgccc tctgagcttg gcgaggatga ttttgaatca aacgcctaaa     720
ggaaacccaa tgcaatttgc taggagattg gactagaga atgtggttag gatattggag     780
gatgcgattt tcgaatatgc aacagtggag agatattgg agaagagagg gaaaggtgaa     840
aatgtggagt atttagtcaa gtggaaggat gggaggata tgaatgggt gaaagcatgg     900 ctgataagtg aggatttggt gagagatttt gaggctggtt tggaatatgc agtggcagag     960
tgtattcttg agaagagaga aggtgaggat gggaagggag aatatttggt taaatggact    1020
```

```
gatattgagg aagctacctg ggaaccggaa gaaaatgttg accccttct aatagaagat    1080 tttgaaaagg gtcaacagaa tgtagtaagt tga                                1113
```

<210> SEQ ID NO 18
<211> LENGTH: 370
<212> TYPE: PRT
<213> ORGANISM: Nicotiana tabacum

<400> SEQUENCE: 18

```
Met Asp Ala Leu Phe Val Asn Ser Ser Leu Ser Arg Leu Lys Leu Lys
1               5                   10                  15

Phe Ser Pro Gln Phe Pro Pro Thr Phe Ser His Gln Pro Phe Ile Arg
            20                  25                  30

Leu Lys Lys Leu Gly Asn Lys Asn Asn Phe Ser Val Phe Ala Thr Leu
        35                  40                  45

Gln Asn Gln Gln Gln Gln Ala Val Ala Ala Glu Glu Glu Glu Pro
    50                  55                  60

Val Leu Phe Glu Asp Tyr Asp Glu Asp Glu Thr Tyr Gly Glu Val Asn
65                  70                  75                  80

Lys Ile Ile Gly Ser Arg Ala Ile Glu Gly Gly Lys Gly Met Glu Tyr
                85                  90                  95

Leu Ile Glu Trp Lys Asp Glu His Ala Pro Thr Trp Val Pro Ser Asp
            100                 105                 110

Tyr Ile Ala Lys Asp Val Val Ala Glu Tyr Glu Thr Pro Trp Trp Asn
        115                 120                 125

Ala Ala Lys Lys Ala Asp Glu Ser Ala Leu Lys Lys Phe Leu Glu Ala
    130                 135                 140

Asp Asp Asp Arg Asp Val Asp Ala Val Asp Glu Asp Gly Arg Thr Ala
145                 150                 155                 160

Leu Leu Phe Val Ser Gly Leu Gly Ser Glu Pro Cys Val Lys Leu Leu
                165                 170                 175

Ala Glu Ala Gly Ala Asp Val Asp Tyr Arg Asp Arg Asn Gly Gly Leu
            180                 185                 190

Thr Ala Leu His Met Ala Ala Gly Tyr Val Lys Pro Gly Val Ala Lys
        195                 200                 205

Leu Leu Ile Asp Leu Gly Ala Asp Pro Glu Val Glu Asp Tyr Arg Gly
    210                 215                 220

Gln Thr Pro Leu Ser Leu Ala Arg Met Ile Leu Asn Gln Thr Pro Lys
225                 230                 235                 240

Gly Asn Pro Met Gln Phe Ala Arg Arg Leu Gly Leu Glu Asn Val Val
                245                 250                 255

Arg Ile Leu Glu Asp Ala Ile Phe Glu Tyr Ala Thr Val Glu Glu Ile
            260                 265                 270

Leu Glu Lys Arg Gly Lys Gly Glu Asn Val Glu Tyr Leu Val Lys Trp
        275                 280                 285

Lys Asp Gly Glu Asp Asn Glu Trp Val Lys Ala Trp Leu Ile Ser Glu
    290                 295                 300

Asp Leu Val Arg Asp Phe Glu Ala Gly Leu Glu Tyr Ala Val Ala Glu
305                 310                 315                 320

Cys Ile Leu Glu Lys Arg Glu Gly Glu Asp Gly Lys Gly Glu Tyr Leu
                325                 330                 335

Val Lys Trp Thr Asp Ile Glu Glu Ala Thr Trp Glu Pro Glu Glu Asn
            340                 345                 350
```

Val Asp Pro Leu Leu Ile Glu Asp Phe Glu Lys Gly Gln Gln Asn Val
                355                 360                 365

Val Ser
    370

<210> SEQ ID NO 19
<211> LENGTH: 1692
<212> TYPE: DNA
<213> ORGANISM: Nicotiana tabacum

<400> SEQUENCE: 19

```
atggaagcca ctgcttcttt ctcctcaact atgtcttccc accatttctt tccactttcc     60
aaagccaccc tctcaacttc taaacttcca ttttctggga ctggttcaac tcattctctt    120
tcattttctt caagaaactc attcactagg gatacatgga gggtgatcaa ttcaaggaat    180
gtggttattt caagaagaga atgcgtggaa gttattagag ctgagatgtt tggacagctc    240
actagtggac ttgaatcagc ttggaataag ctcaaaggag aagaggtttt gaccaaggaa    300
aacattgtgg aacctatgag agacatcagg agggctcttt tggaagctga tgttagtctc    360
cctgttgtca aaggtttgt tcagtctgtt agtgacgaag ccgtggggac tggcttgatt    420
cgaggagtaa gaccagatca gcaactagtt aaaattgtac gagacgagct tgtgaaactg    480
atgggtggag aggtctctga actggtattt gctaaatctg gacccaccat aatactattg    540
gccggtctac aaggtgttgg aaagacaact gttagcgcaa agttagcttt tatctaaag    600
aagcagggta agagttgcat gctgattgct ggagacgtgt atagacctgc tgctattgac    660
caacttgtta ttttgggtga acaggttgat gtgcctgttt atgcagcagg aacagacgta    720
aaacctgcag aaatagcccg tcaaggatta aagaggcca aagaaagaa tgtagatgta    780
gtcataatgg atacagctgg acgacttcag atagataaag ctatgatgga tgaattaaaa    840
gaggtgaaac gggtactgaa ccccacagag gttttgcttg ttgtggatgc aatgactggc    900
caagaagctg cagcttttggt cacaacattc aatctcgaaa ttggaattac tggtgccatt    960
atgacaaagc tagatgggga ttctagggt ggagcagctt taagtgtcaa ggaggtatca   1020
ggaaagccaa ttaagctcgt aggaagaggt gaacgtatgg aggaccttga acctttctat   1080
cctgaccgca tggctggacg tatttaggg atgggagatg ttctgtcgtt tgttgaaaaa   1140
gcccaagaag ttatgaaaca gaagatgca gaagatttgc agaagaagat catgagtgca   1200
aaatttgatt tcaatgactt cctgaagcaa actcgtgcag ttgctcaaat gggtaccatg   1260
tcccgcgttc tcggaatgat tcctggcatg ggaaaggtta ctcctgcaca aattcgagag   1320
gcagagaaga gcttaataat aatggagtca atgatagaag tcatgacacc agaggagaag   1380
gagaaaccag aactgttagc agaatctcct agtagaagga aacgtattgc tcaagagtcc   1440
gggaaaactg agcagcaggt gagtcaactt gttgctcaac ttttcaaat gcgtgtacgt   1500
atgaagaatt tgatgggtgt tatgcaaggt ggttccatac ctgcactgag taatcttgag   1560
gaggcactta aaactgaaca gaaggctcct cctggtactg caaggaggaa gcgaaggtca   1620
gaatcaagaa agcaatttgc agactcggga tcaactagac ctggccctcg tggttttggg   1680
gccaagaact aa                                                      1692
```

<210> SEQ ID NO 20
<211> LENGTH: 563
<212> TYPE: PRT
<213> ORGANISM: Nicotiana tabacum

<400> SEQUENCE: 20

-continued

```
Met Glu Ala Thr Ala Ser Phe Ser Ser Thr Met Ser Ser His His Phe
1               5                   10                  15

Phe Pro Leu Ser Lys Ala Thr Leu Ser Thr Ser Lys Leu Pro Phe Ser
                20                  25                  30

Gly Thr Gly Ser Thr His Ser Leu Ser Phe Ser Ser Arg Asn Ser Phe
            35                  40                  45

Thr Arg Asp Thr Trp Arg Val Ile Asn Ser Arg Asn Val Val Ile Ser
        50                  55                  60

Arg Arg Glu Met Arg Gly Val Ile Arg Ala Glu Met Phe Gly Gln Leu
65                  70                  75                  80

Thr Ser Gly Leu Glu Ser Ala Trp Asn Lys Leu Lys Gly Glu Glu Val
                85                  90                  95

Leu Thr Lys Glu Asn Ile Val Glu Pro Met Arg Asp Ile Arg Arg Ala
                100                 105                 110

Leu Leu Glu Ala Asp Val Ser Leu Pro Val Val Arg Arg Phe Val Gln
            115                 120                 125

Ser Val Ser Asp Glu Ala Val Gly Thr Gly Leu Ile Arg Gly Val Arg
        130                 135                 140

Pro Asp Gln Gln Leu Val Lys Ile Val Arg Asp Glu Leu Val Lys Leu
145                 150                 155                 160

Met Gly Gly Glu Val Ser Glu Leu Val Phe Ala Lys Ser Gly Pro Thr
                165                 170                 175

Ile Ile Leu Leu Ala Gly Leu Gln Gly Val Gly Lys Thr Thr Val Ser
                180                 185                 190

Ala Lys Leu Ala Leu Tyr Leu Lys Lys Gln Gly Lys Ser Cys Met Leu
            195                 200                 205

Ile Ala Gly Asp Val Tyr Arg Pro Ala Ala Ile Asp Gln Leu Val Ile
        210                 215                 220

Leu Gly Glu Gln Val Asp Val Pro Val Tyr Ala Ala Gly Thr Asp Val
225                 230                 235                 240

Lys Pro Ala Glu Ile Ala Arg Gln Gly Leu Glu Ala Lys Arg Lys
                245                 250                 255

Asn Val Asp Val Val Ile Met Asp Thr Ala Gly Arg Leu Gln Ile Asp
                260                 265                 270

Lys Ala Met Met Asp Glu Leu Lys Glu Val Lys Arg Val Leu Asn Pro
            275                 280                 285

Thr Glu Val Leu Leu Val Val Asp Ala Met Thr Gly Gln Glu Ala Ala
        290                 295                 300

Ala Leu Val Thr Thr Phe Asn Leu Glu Ile Gly Ile Thr Gly Ala Ile
305                 310                 315                 320

Met Thr Lys Leu Asp Gly Asp Ser Arg Gly Gly Ala Ala Leu Ser Val
                325                 330                 335

Lys Glu Val Ser Gly Lys Pro Ile Lys Leu Val Gly Arg Gly Glu Arg
                340                 345                 350

Met Glu Asp Leu Glu Pro Phe Tyr Pro Asp Arg Met Ala Gly Arg Ile
            355                 360                 365

Leu Gly Met Gly Asp Val Leu Ser Phe Val Glu Lys Ala Gln Glu Val
        370                 375                 380

Met Lys Gln Glu Asp Ala Glu Asp Leu Gln Lys Lys Ile Met Ser Ala
385                 390                 395                 400

Lys Phe Asp Phe Asn Asp Phe Leu Lys Gln Thr Arg Ala Val Ala Gln
                405                 410                 415
```

```
Met Gly Thr Met Ser Arg Val Leu Gly Met Ile Pro Gly Met Gly Lys
                420                 425                 430
Val Thr Pro Ala Gln Ile Arg Glu Ala Glu Lys Ser Leu Ile Ile Met
            435                 440                 445
Glu Ser Met Ile Glu Val Met Thr Pro Glu Glu Lys Glu Lys Pro Glu
        450                 455                 460
Leu Leu Ala Glu Ser Pro Ser Arg Arg Lys Arg Ile Ala Gln Glu Ser
465                 470                 475                 480
Gly Lys Thr Glu Gln Gln Val Ser Gln Leu Val Ala Gln Leu Phe Gln
                485                 490                 495
Met Arg Val Arg Met Lys Asn Leu Met Gly Val Met Gln Gly Gly Ser
            500                 505                 510
Ile Pro Ala Leu Ser Asn Leu Glu Glu Ala Leu Lys Thr Glu Gln Lys
        515                 520                 525
Ala Pro Pro Gly Thr Ala Arg Arg Lys Arg Arg Ser Glu Ser Arg Lys
    530                 535                 540
Gln Phe Ala Asp Ser Gly Ser Thr Arg Pro Gly Pro Arg Gly Phe Gly
545                 550                 555                 560
Ala Lys Asn

<210> SEQ ID NO 21
<211> LENGTH: 1605
<212> TYPE: DNA
<213> ORGANISM: Nicotiana tabacum

<400> SEQUENCE: 21
atgtccgcca ttgctacttc tgctgctctc tcttttcctt tctctttctg ccgttctacc        60
aagacttttg ctacaagaaa gtgtttcaaa gggggatttg gagtgtttgc agtgtatgag       120
gaggcaggtg agttaacaaa caagaaaagc tcctggttga cactctttga tgtggaagat       180
ccaaggtcaa aatttcctca gtctaaaggc aagttcctgg atgcaaatca agctttagaa       240
gttgctagat ttgatataca atattgtgat tggcgagctc ggcaagatgt attaaccata       300
atgctcctgc acgaaaaggt tgtggaagta ttgaatcctc tggcacgtga gtacaaatct       360
attggaacca tgaagaagga actagcagag ttacaaggag cactttctca ggctcataaa       420
gaggtacata tatctgaggt gcgggtttct gctgctttag ataagctagc tcacatggaa       480
gcattggtta tgataggct gcttccggag aggagtgcag aagaatcaga ttgcccgtct       540
tcctccaccg gtacgtctac agtatctaga gatactgtta aaggcaagca gcctaggaga       600 acctcaatg tgtcaggtcc ggtccaagat tacagctctc atttgaagaa ctttggtat       660 cctgtcgctt tttctgctga tgttaaggaa gacacaatga caccaattga ttgctttgag       720
gaaccatggg tgattttcg tgggaaagat ggaaaacctg atgtgtccg aacacatgt       780 gcacatagag cctgccccct tcatttgggt tcagttaatg agggtcgcat ccaatgtcct       840
tatcatgggt gggaatattc aacagacgga aaatgtgaga aatgccatc aactaaattt       900 ctgaatgtca agatcaaagc tctgccatgc tttgagcaag agggaatgat atggatttgg       960
cctggaaatg atcctcctgc agctactctt ccttctttac tgccaccttc tggatttcaa      1020
atccatgcag agattgttat tgaacttcca gtgaacatg gctacttttt ggacaatctg      1080
ttggatcttg cacatgctcc tttcacccat acgtctacat ttgctaaagg atggactgtc      1140
ccaagctttg taaaatttt gactcctgca tctggtcttc aaggatattg ggatccctat      1200
ccaatagata tggaatttcg accaccttgt atagttctat caaccattgg aatctcaaag      1260
```

-continued

```
ccaggcaagt tggaagggca gagtaccaaa gagtgctcta cacacctaca ccaacttcat    1320
gtatgtttac ctgcatctaa acagaagaca aggttgttat ataggatgtc actggatttt    1380
gctcccgtgc taaaacacat ccctttcatg caatacgtgt ggaggcattt tgctgaacag    1440
gttttaaacg aagacctacg gcttgtgatt ggtcagcaag agcggatgct caatggtgct    1500
aacatttgga acctgcctgt gtcatacgat aagctaggag tgaggtatag gatatggaga    1560
gatgctgtag agagtggagc aaagcaattg ccattcagca aatga                    1605
```

```
<210> SEQ ID NO 22
<211> LENGTH: 534
<212> TYPE: PRT
<213> ORGANISM: Nicotiana tabacum

<400> SEQUENCE: 22
```

| | | | | | | | | | | | | | | | |
|---|---|---|---|---|---|---|---|---|---|---|---|---|---|---|---|
| Met | Ser | Ala | Ile | Ala | Thr | Ser | Ala | Ala | Leu | Ser | Phe | Pro | Phe | Ser | Phe |
| 1 | | | | 5 | | | | | 10 | | | | | 15 | |
| Cys | Arg | Ser | Thr | Lys | Thr | Phe | Ala | Thr | Arg | Lys | Cys | Phe | Lys | Gly | Gly |
| | | | 20 | | | | | 25 | | | | | 30 | | |
| Phe | Gly | Val | Phe | Ala | Val | Tyr | Glu | Glu | Ala | Gly | Glu | Leu | Thr | Asn | Lys |
| | | 35 | | | | | 40 | | | | | 45 | | | |
| Lys | Ser | Ser | Trp | Leu | Thr | Leu | Phe | Asp | Val | Glu | Asp | Pro | Arg | Ser | Lys |
| | 50 | | | | | 55 | | | | | 60 | | | | |
| Phe | Pro | Gln | Ser | Lys | Gly | Lys | Phe | Leu | Asp | Ala | Asn | Gln | Ala | Leu | Glu |
| 65 | | | | | 70 | | | | | 75 | | | | | 80 |
| Val | Ala | Arg | Phe | Asp | Ile | Gln | Tyr | Cys | Asp | Trp | Arg | Ala | Arg | Gln | Asp |
| | | | | 85 | | | | | 90 | | | | | 95 | |
| Val | Leu | Thr | Ile | Met | Leu | Leu | His | Glu | Lys | Val | Glu | Val | Leu | Asn | |
| | | | 100 | | | | | 105 | | | | | 110 | | |
| Pro | Leu | Ala | Arg | Glu | Tyr | Lys | Ser | Ile | Gly | Thr | Met | Lys | Lys | Glu | Leu |
| | | | 115 | | | | | 120 | | | | | 125 | | |
| Ala | Glu | Leu | Gln | Gly | Ala | Leu | Ser | Gln | Ala | His | Lys | Glu | Val | His | Ile |
| | 130 | | | | | 135 | | | | | 140 | | | | |
| Ser | Glu | Val | Arg | Val | Ser | Ala | Ala | Leu | Asp | Lys | Leu | Ala | His | Met | Glu |
| 145 | | | | | 150 | | | | | 155 | | | | | 160 |
| Ala | Leu | Val | Asn | Asp | Arg | Leu | Leu | Pro | Glu | Arg | Ser | Ala | Glu | Glu | Ser |
| | | | | 165 | | | | | 170 | | | | | 175 | |
| Asp | Cys | Pro | Ser | Ser | Ser | Thr | Gly | Thr | Ser | Thr | Val | Ser | Arg | Asp | Thr |
| | | | 180 | | | | | 185 | | | | | 190 | | |
| Val | Lys | Gly | Lys | Gln | Pro | Arg | Arg | Thr | Leu | Asn | Val | Ser | Gly | Pro | Val |
| | | 195 | | | | | 200 | | | | | 205 | | | |
| Gln | Asp | Tyr | Ser | Ser | His | Leu | Lys | Asn | Phe | Trp | Tyr | Pro | Val | Ala | Phe |
| | 210 | | | | | 215 | | | | | 220 | | | | |
| Ser | Ala | Asp | Val | Lys | Glu | Asp | Thr | Met | Thr | Pro | Ile | Asp | Cys | Phe | Glu |
| 225 | | | | | 230 | | | | | 235 | | | | | 240 |
| Glu | Pro | Trp | Val | Ile | Phe | Arg | Gly | Lys | Asp | Gly | Lys | Pro | Gly | Cys | Val |
| | | | | 245 | | | | | 250 | | | | | 255 | |
| Arg | Asn | Thr | Cys | Ala | His | Arg | Ala | Cys | Pro | Leu | His | Leu | Gly | Ser | Val |
| | | | 260 | | | | | 265 | | | | | 270 | | |
| Asn | Glu | Gly | Arg | Ile | Gln | Cys | Pro | Tyr | His | Gly | Trp | Glu | Tyr | Ser | Thr |
| | | 275 | | | | | 280 | | | | | 285 | | | |
| Asp | Gly | Lys | Cys | Glu | Lys | Met | Pro | Ser | Thr | Lys | Phe | Leu | Asn | Val | Lys |
| | 290 | | | | | 295 | | | | | 300 | | | | |
| Ile | Lys | Ala | Leu | Pro | Cys | Phe | Glu | Gln | Glu | Gly | Met | Ile | Trp | Ile | Trp |
| 305 | | | | | 310 | | | | | 315 | | | | | 320 |

```
Pro Gly Asn Asp Pro Ala Ala Thr Leu Pro Ser Leu Leu Pro Pro
                325                 330                 335

Ser Gly Phe Gln Ile His Ala Glu Ile Val Ile Glu Leu Pro Val Glu
            340                 345                 350

His Gly Leu Leu Leu Asp Asn Leu Leu Asp Leu Ala His Ala Pro Phe
                355                 360                 365

Thr His Thr Ser Thr Phe Ala Lys Gly Trp Thr Val Pro Ser Phe Val
    370                 375                 380

Lys Phe Leu Thr Pro Ala Ser Gly Leu Gln Gly Tyr Trp Asp Pro Tyr
385                 390                 395                 400

Pro Ile Asp Met Glu Phe Arg Pro Pro Cys Ile Val Leu Ser Thr Ile
                405                 410                 415

Gly Ile Ser Lys Pro Gly Lys Leu Glu Gly Gln Ser Thr Lys Glu Cys
            420                 425                 430

Ser Thr His Leu His Gln Leu His Val Cys Leu Pro Ala Ser Lys Gln
                435                 440                 445

Lys Thr Arg Leu Leu Tyr Arg Met Ser Leu Asp Phe Ala Pro Val Leu
    450                 455                 460

Lys His Ile Pro Phe Met Gln Tyr Val Trp Arg His Phe Ala Glu Gln
465                 470                 475                 480

Val Leu Asn Glu Asp Leu Arg Leu Val Ile Gly Gln Gln Arg Met
                485                 490                 495

Leu Asn Gly Ala Asn Ile Trp Asn Leu Pro Val Ser Tyr Asp Lys Leu
            500                 505                 510

Gly Val Arg Tyr Arg Ile Trp Arg Asp Ala Val Glu Ser Gly Ala Lys
    515                 520                 525

Gln Leu Pro Phe Ser Lys
    530

<210> SEQ ID NO 23
<211> LENGTH: 1605
<212> TYPE: DNA
<213> ORGANISM: Nicotiana tabacum

<400> SEQUENCE: 23
atgtccgcca ttgctacttc tgctgctctc tcttttcctt tctcttttg ccgttctacc     60 aagactttta ctacaagaaa gtgtttcaaa gggggatttg gagtgtttgc agtgtatgag   120
gaggcaggtg agttaacaaa caagaaaagc tcctggttga cactctttga tgtggaagat   180
ccaaggtcaa aatttcctca gtctaaaggc aagttcctgg atgcaaatca agctttagaa   240
gttgctagat ttgatatgca atattgtgat ggcgagctc ggcaagacgt acttacaata   300
atgctcctgc atgaaaaggt tgtggaagta ttgaatcctc tagctcgtga atataaatct   360
attggaacca tgaagaagga actcgcggag ttacaagaag aactgtctcg ggctcacaaa   420
gaggtacata tatctgaggt gcgggtttct gctgctttag ataagctagc tcacatggaa   480
gcattggtta atgataggct gcttccggag aggagtacag aagaatcaga ttccccatct   540
tcctccaccg gtacgtctac agtatctaga gataatgcta aaagcaagca gcctaggaga   600
accctcaatg tgtcaggtcc cgtccaagat tacagctcct atttgaagaa cttttggtat   660
cctgtggctt tttctgctga tgttaaggaa gataccatga caccaattga ttgctttgag   720
gaaccgtggg tgattttcg tgggaaagat ggaaaacctg atgtgtccaa gaacacatgt   780
gcacatagag cttgccccct tcatttgggt tcagtgaatg agggtcgcat acaatgtcct   840
```

-continued

```
tatcacgggt gggaatattc aacagacgga aaatgtgaga aaatgccatc aacaaaattt      900
ctgaatgtca agatcaaagc tctgccatgc tttgagcaag agggaatgat atggatttgg      960
cctggaaacg atcctcctgc agctactctt ccttctttgc taccaccttc tggatttcaa     1020
atccatgcag agattgtcat ggaacttccg gtggaacatg ggctactttt ggacaatctg     1080
ttggatcttg cacatgctcc tttcactcat acgtctacat ttgctaaagg atggactgtc     1140
ccaagctttg taaaattttt gactcctgcg tctggtctgc aaggatattg ggatccatat     1200
ccaatagata tggaatttcg accgccttgt atggttctgt caaccattgg aatctcaaag     1260
ccgggcaaat tggaagggca gagtatcaaa gagtgctcta cacaccttca ccaacttcat     1320
gtatgtttac ctgcatctaa acagaagaca aggttgttat ataggatgtc actggatttt     1380
gctcctgttc taaaacacat ccctttcatg caatacgtgt ggaggcattt tgctgaacag     1440
gttttaaatg aagacctacg gcttgtgatt ggtcagcaag aacggatgct caatggtgct     1500
aacatttgga acctgcctgt gtcatacgat aagctaggag tgaggtatag aatatggaga     1560
gacgctgtag agagtggagc aaagcagttg ccgttcagca aatga                     1605
```

<210> SEQ ID NO 24
<211> LENGTH: 534
<212> TYPE: PRT
<213> ORGANISM: Nicotiana tabacum

<400> SEQUENCE: 24

```
Met Ser Ala Ile Ala Thr Ser Ala Ala Leu Ser Phe Pro Phe Ser Phe
1               5                   10                  15

Cys Arg Ser Thr Lys Thr Phe Thr Arg Lys Cys Phe Lys Gly Gly
            20                  25                  30

Phe Gly Val Phe Ala Val Tyr Glu Glu Ala Gly Glu Leu Thr Asn Lys
        35                  40                  45

Lys Ser Ser Trp Leu Thr Leu Phe Asp Val Glu Asp Pro Arg Ser Lys
    50                  55                  60

Phe Pro Gln Ser Lys Gly Lys Phe Leu Asp Ala Asn Gln Ala Leu Glu
65                  70                  75                  80

Val Ala Arg Phe Asp Met Gln Tyr Cys Asp Trp Arg Ala Arg Gln Asp
                85                  90                  95

Val Leu Thr Ile Met Leu Leu His Glu Lys Val Glu Val Leu Asn
            100                 105                 110

Pro Leu Ala Arg Glu Tyr Lys Ser Ile Gly Thr Met Lys Lys Glu Leu
        115                 120                 125

Ala Glu Leu Gln Glu Glu Leu Ser Arg Ala His Lys Glu Val His Ile
    130                 135                 140

Ser Glu Val Arg Val Ser Ala Ala Leu Asp Lys Leu Ala His Met Glu
145                 150                 155                 160

Ala Leu Val Asn Asp Arg Leu Leu Pro Glu Arg Ser Thr Glu Glu Ser
                165                 170                 175

Asp Ser Pro Ser Ser Thr Gly Thr Ser Thr Val Ser Arg Asp Asn
            180                 185                 190

Ala Lys Ser Lys Gln Pro Arg Arg Thr Leu Asn Val Ser Gly Pro Val
        195                 200                 205

Gln Asp Tyr Ser Ser Tyr Leu Lys Asn Phe Trp Tyr Pro Val Ala Phe
    210                 215                 220

Ser Ala Asp Val Lys Glu Asp Thr Met Thr Pro Ile Asp Cys Phe Glu
225                 230                 235                 240
```

-continued

```
Glu Pro Trp Val Ile Phe Arg Gly Lys Asp Gly Lys Pro Gly Cys Val
                245                 250                 255
Gln Asn Thr Cys Ala His Arg Ala Cys Pro Leu His Leu Gly Ser Val
            260                 265                 270
Asn Glu Gly Arg Ile Gln Cys Pro Tyr His Gly Trp Glu Tyr Ser Thr
        275                 280                 285
Asp Gly Lys Cys Glu Lys Met Pro Ser Thr Lys Phe Leu Asn Val Lys
    290                 295                 300
Ile Lys Ala Leu Pro Cys Phe Glu Gln Glu Gly Met Ile Trp Ile Trp
305                 310                 315                 320
Pro Gly Asn Asp Pro Ala Ala Thr Leu Pro Ser Leu Leu Pro Pro
                325                 330                 335
Ser Gly Phe Gln Ile His Ala Glu Ile Val Met Glu Leu Pro Val Glu
            340                 345                 350
His Gly Leu Leu Leu Asp Asn Leu Asp Leu Ala His Ala Pro Phe
        355                 360                 365
Thr His Thr Ser Thr Phe Ala Lys Gly Trp Thr Val Pro Ser Phe Val
    370                 375                 380
Lys Phe Leu Thr Pro Ala Ser Gly Leu Gln Gly Tyr Trp Asp Pro Tyr
385                 390                 395                 400
Pro Ile Asp Met Glu Phe Arg Pro Pro Cys Met Val Leu Ser Thr Ile
                405                 410                 415
Gly Ile Ser Lys Pro Gly Lys Leu Glu Gly Gln Ser Ile Lys Glu Cys
            420                 425                 430
Ser Thr His Leu His Gln Leu His Val Cys Leu Pro Ala Ser Lys Gln
        435                 440                 445
Lys Thr Arg Leu Leu Tyr Arg Met Ser Leu Asp Phe Ala Pro Val Leu
    450                 455                 460
Lys His Ile Pro Phe Met Gln Tyr Val Trp Arg His Phe Ala Glu Gln
465                 470                 475                 480
Val Leu Asn Glu Asp Leu Arg Leu Val Ile Gly Gln Gln Glu Arg Met
                485                 490                 495
Leu Asn Gly Ala Asn Ile Trp Asn Leu Pro Val Ser Tyr Asp Lys Leu
            500                 505                 510
Gly Val Arg Tyr Arg Ile Trp Arg Asp Ala Val Glu Ser Gly Ala Lys
        515                 520                 525
Gln Leu Pro Phe Ser Lys
    530

<210> SEQ ID NO 25
<211> LENGTH: 1596
<212> TYPE: DNA
<213> ORGANISM: Nicotiana tabacum

<400> SEQUENCE: 25
atgacagcca ttactactgc tctttctttt cctttctctt tgtgccgctc tactaagtct      60
tatactagaa agtatgtcaa agggagcttt ggagtgtttg cagtatatgg ggaggagggt     120
gggatgccag ataagaaaag ttcctggttg acactcttta atgtggaaga tccaaggtct     180
aaagttccac aaattaaagg caaattcttg gatgcaaatc aagctttgga agttgctaga     240
tatgatctac aatactgtga ttggcgagct cggcaagatg tacttacaat catgctgctg     300
catgaaaagg ttgtggaagt gttgaaccct ctagcacgtg aatacaaatc tattggaacc     360
atgaaaaagg aacttgcaga gttgcaagga gagctttctc aggcccacaa ccaggtacat     420
```

```
atatctgagg cccgggtttc tgctgctttg ataagctag cttacatgga agagttggtt    480
aatgataggc ttctgcaaga gagaagcacg gcagaatcag attgctcgtc ctcctctgcc    540
agtacgtcaa cagcattatt ggatactgtt aaaagcaagc aaccccgaag aaccctgagt    600
gtgtcaggtc ctgtccaaga ttacagttcc cgtttgaaga acttttggta ccctgttgct    660
ttctccgcag atcttaagga tgacaccatg ttaccgattg attgctttga gcaaccatgg    720
gtgatctttc gcgggaatga tggaaaacct ggatgtgtac agaatacgtg tgcacataga    780
gcctgccccc ttgatcttgg ctcagtgaaa gagggacgca ttcagtgccc ttatcacgga    840
tgggaatact caactgatgg gaagtgtgag aaaatgccat caacacgatt actgaatgta    900
aagatcaaag cactgccctg ctttgagcaa gagggaatga tatggatttg ccaggaaat    960 gatccccctg cagctaccct tccttcttta ctaccgcctt ctggatttca atccatgcg    1020 gagatagtca tggaacttcc agtggaacat gggctattat tagacaattt attggatctt    1080
gcacatgctc ctttcaccca tacatcaacc tttgctaaag gatggagtgt cccaagattg    1140
gtgaagtttt tgactcctgc ttctggtctg caaggatatt gggatcctta tccaatagat    1200
atggaattta gaccaccttg tatggtttta tcaaccattg gaatctcaaa gccaggcaaa    1260
ttggaggggc agagtaccaa gcagtgttgt acacaccttc atcaacttca tgtttgctta    1320
cctgcatcac gacacaagac acggttatta tataggatgt cactggattt tgctcccctg    1380
ctgaaacaca tccctttcat gcaatatgtt tggagacatt tgccgaaaca ggttttaaat    1440
gaagacctac ggcttgtgtt gggccagcag gatcgcatgc tcaatggcgc caatatttgg    1500
aacttgccag tgtcttacga taagctaggt gtgaggtata aatatggag agatgctgta    1560 gatagtggag caaagcatct accattcagc aaataa                              1596

<210> SEQ ID NO 26
<211> LENGTH: 531
<212> TYPE: PRT
<213> ORGANISM: Nicotiana tabacum

<400> SEQUENCE: 26

Met Thr Ala Ile Thr Thr Ala Leu Ser Phe Pro Phe Ser Leu Cys Arg
1               5                   10                  15

Ser Thr Lys Ser Tyr Thr Arg Lys Tyr Val Lys Gly Ser Phe Gly Val
                20                  25                  30

Phe Ala Val Tyr Gly Glu Glu Gly Met Pro Asp Lys Lys Ser Ser
            35                  40                  45

Trp Leu Thr Leu Phe Asn Val Glu Asp Pro Arg Ser Lys Val Pro Gln
50                  55                  60

Ile Lys Gly Lys Phe Leu Asp Ala Asn Gln Ala Leu Glu Val Ala Arg
65                  70                  75                  80

Tyr Asp Leu Gln Tyr Cys Asp Trp Arg Ala Arg Gln Asp Val Leu Thr
                85                  90                  95

Ile Met Leu Leu His Glu Lys Val Val Glu Val Leu Asn Pro Leu Ala
            100                 105                 110

Arg Glu Tyr Lys Ser Ile Gly Thr Met Lys Lys Glu Leu Ala Glu Leu
        115                 120                 125

Gln Gly Glu Leu Ser Gln Ala His Asn Gln Val His Ile Ser Glu Ala
    130                 135                 140

Arg Val Ser Ala Ala Leu Asp Lys Leu Ala Tyr Met Glu Glu Leu Val
145                 150                 155                 160

Asn Asp Arg Leu Leu Gln Glu Arg Ser Thr Ala Glu Ser Asp Cys Ser
```

165                 170                 175
Ser Ser Ser Ala Ser Thr Ser Thr Ala Leu Leu Asp Thr Val Lys Ser
            180                 185                 190

Lys Gln Pro Arg Arg Thr Leu Ser Val Ser Gly Pro Val Gln Asp Tyr
        195                 200                 205

Ser Ser Arg Leu Lys Asn Phe Trp Tyr Pro Val Ala Phe Ser Ala Asp
    210                 215                 220

Leu Lys Asp Asp Thr Met Leu Pro Ile Asp Cys Phe Glu Gln Pro Trp
225                 230                 235                 240

Val Ile Phe Arg Gly Asn Asp Gly Lys Pro Gly Cys Val Gln Asn Thr
                245                 250                 255

Cys Ala His Arg Ala Cys Pro Leu Asp Leu Gly Ser Val Lys Glu Gly
            260                 265                 270

Arg Ile Gln Cys Pro Tyr His Gly Trp Glu Tyr Ser Thr Asp Gly Lys
        275                 280                 285

Cys Glu Lys Met Pro Ser Thr Arg Leu Leu Asn Val Lys Ile Lys Ala
    290                 295                 300

Leu Pro Cys Phe Glu Gln Glu Gly Met Ile Trp Ile Trp Pro Gly Asn
305                 310                 315                 320

Asp Pro Pro Ala Ala Thr Leu Pro Ser Leu Leu Pro Pro Ser Gly Phe
                325                 330                 335

Gln Ile His Ala Glu Ile Val Met Glu Leu Pro Val Glu His Gly Leu
            340                 345                 350

Leu Leu Asp Asn Leu Leu Asp Leu Ala His Ala Pro Phe Thr His Thr
        355                 360                 365

Ser Thr Phe Ala Lys Gly Trp Ser Val Pro Arg Leu Val Lys Phe Leu
    370                 375                 380

Thr Pro Ala Ser Gly Leu Gln Gly Tyr Trp Asp Pro Tyr Pro Ile Asp
385                 390                 395                 400

Met Glu Phe Arg Pro Pro Cys Met Val Leu Ser Thr Ile Gly Ile Ser
                405                 410                 415

Lys Pro Gly Lys Leu Glu Gly Gln Ser Thr Lys Gln Cys Cys Thr His
            420                 425                 430

Leu His Gln Leu His Val Cys Leu Pro Ala Ser Arg His Lys Thr Arg
        435                 440                 445

Leu Leu Tyr Arg Met Ser Leu Asp Phe Ala Pro Leu Leu Lys His Ile
    450                 455                 460

Pro Phe Met Gln Tyr Val Trp Arg His Phe Ala Glu Gln Val Leu Asn
465                 470                 475                 480

Glu Asp Leu Arg Leu Val Leu Gly Gln Gln Asp Arg Met Leu Asn Gly
                485                 490                 495

Ala Asn Ile Trp Asn Leu Pro Val Ser Tyr Asp Lys Leu Gly Val Arg
            500                 505                 510

Tyr Arg Ile Trp Arg Asp Ala Val Asp Ser Gly Ala Lys His Leu Pro
        515                 520                 525

Phe Ser Lys
    530

<210> SEQ ID NO 27
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
ggatccatgg cttctctatt atcttctcgt ctcccacgtc atctttcctc taataaaccg    60
gtactcccac catcaagctc cggttcaaat ctccttcaca acttcacata taaaacccgg   120
ttcgatcaat cccggttcaa atgctcagct ggtggaacgg ggttcttcac gaagttgggt   180
cgtttgctga agagaaagc aaagagcgac gtggagaaac tgttctcagg attctcaaaa    240
actcgagaca atttagcagt tatagatgaa ctcctccttt actggtaata agatcttcaa   300
cacctacacc attttttaa tcactactac ccattgcatt gaacaaactt ccaagttctt    360
cttagcttca gattaagaaa gtacccttc ttggctttgt tgatgtggta ccattgtcca    420
ttgtcttgtg tgtttccacc agtaaaggag gagttcatct ataactgcta aattgtctcg   480
agttttgag aatcctgaga acagtttctc cacgtcgctc tttgctttct ctttcagcaa    540
acgacccaac ttcgtgaaga accccgttcc accagctgag catttgaacc gggattgatc   600
gaaccgggtt ttatatgtga agttgtgaag gagatttgaa ccggagcttg atggtgggag   660
taccggttta ttagaggaaa gatgacgtgg gagacgagaa gataatagag aagccattct   720
aga                                                                 723
```

<210> SEQ ID NO 28
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
ggatccggga aaggaatgga gtacttgata gagtggaaag acgaacatgc cccaacgtgg    60
gtcccctctg attacattgc taaagatgtt gtggccgagt acgaaactcc ttggtggaat   120
gcggctaaaa aggccgacga atccgctctt agggaactcc tagaaactga cgacgacaga   180
gatgtggacg cagtagatga ggatggacgt acggctttgc tctttgtctc gggtctgggg   240
tccgagccgt gtgtcaagct gctagctgaa gccggcgctg acgtggacta tcgcgatagg   300
aatggctaat aagatcttca cacctacac catttttta atcactacta cccattgcat    360
tgaacaaact tccaagttct tcttagcttc agattaagaa agtacccttt cttggctttg   420
ttgatgtggt accattgtcc attgtcttgt gtgtttccag ccattcctat cgcgatagtc   480
cacgtcagcg ccggcttcag ctagcagctt gacacacggc tcggacccca gacccgagac   540
aaagagcaaa gccgtacgtc catcctcatc tactgcgtcc acatctctgt cgtcgtcagt   600
ttctaggagt tccctaagag cggattcgtc ggcctttta gccgcattcc accaaggagt   660
ttcgtactcg gccacaacat ctttagcaat gtaatcagag gggacccacg ttggggcatg   720
ttcgtctttc cactctatca agtactccat tcctttccct ctaga                   765
```

<210> SEQ ID NO 29
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
ggatccatgg aagccactgc ttctttctcc tcaactatgt cttcccacca tttctttcca    60
```

```
ctttccaaag ccaccctctc aacttctaaa cttccatttt ctgggactgg ttcaactcat      120
tctctttcat tttcttcaag aaactcattc actagggata catggagggt gatcaattca      180
aggaatgtgg ttatttcaag aagagaaatg cgtggagtta ttagagctga gatgtttgga      240
cagctcacta gtggacttga atcagcttgg aataagctca aaggagaaga ggttttgtaa      300
taagatcttc aacacctaca ccatttttt aatcactact acccattgca ttgaacaaac       360
ttccaagttc ttcttagctt cagattaaga aagtacccctt tcttggcttt gttgatgtgg     420
taccattgtc cattgtcttg tgtgtttcca caaaacctct tctcctttga gcttattcca      480
agctgattca agtccactag tgagctgtcc aaacatctca gctctaataa ctccacgcat      540
ttctcttctt gaaataacca cattccttga attgatcacc ctccatgtat ccctagtgaa      600
tgagtttctt gaagaaaatg aaagagaatg agttgaacca gtcccagaaa atggaagttt     660
agaagttgag agggtggctt tggaaagtgg aaagaaatgg tgggaagaca tagttgagga    720
gaaagaagca gtggcttcca ttctaga                                          747

<210> SEQ ID NO 30
<211> LENGTH: 987
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ggatccgagg caggtgagtt aacaaacaag aaaagctcct ggttgacact ctttgatgtg       60
gaagatccaa ggtcaaaatt tcctcagtct aaaggcaagt tcctggatgc aaatcaagct     120
ttagaagttg ctagatttga tatacaatat tgtgattggc gagctcggca agatgtatta     180
accataatgc tcctgcacga aaaggttgtg gaagtattga atcctctggc acgtgagtac    240
aaatctattg gaaccatgaa aaaggaactt gcagagttgc aaggagagct ttctcaggcc    300
cacaaccagg tacatatatc tgaggcccgg gtttctgctg ctttggataa gctagcttac   360
atggaagagt tggttaatga taggcttctg caagagagaa gcacggcaga atcagattaa    420
taagatcttc aacacctaca ccatttttt aatcactact acccattgca ttgaacaaac     480
ttccaagttc ttcttagctt cagattaaga aagtacccctt tcttggcttt gttgatgtgg    540
taccattgtc cattgtcttg tgtgtttcca atctgattct gccgtgcttc tctcttgcag    600
aagcctatca ttaaccaact cttccatgta agctagctta ccaaagcag cagaaacccg    660 ggcctcagat atatgtacct ggttgtgggc ctgagaaagc tctccttgca actctgcaag   720 ttccttttc atggttccaa tagatttgta ctcacgtgcc agaggattca atacttccac    780 aacctttcg tgcaggagca ttatggttaa tacatcttgc cgagctcgcc aatcacaata    840
ttgtatatca aatctagcaa cttctaaagc ttgatttgca tccaggaact gcctttaga    900 ctgaggaaat tttgacccttg gatcttccac atcaaagagt gtcaaccagg agcttttctt   960
gtttgttaac tcacctgcct ctctaga                                         987

<210> SEQ ID NO 31
<211> LENGTH: 3155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: MISC_FEATURE
```

```
<222> LOCATION: (1)..(480)
<223> OTHER INFORMATION: pCSVMV Promoter
<220> FEATURE:
<221> NAME/KEY: MISC_FEATURE
<222> LOCATION: (523)..(551)
<223> OTHER INFORMATION: Cloning region
<220> FEATURE:
<221> NAME/KEY: MISC_FEATURE
<222> LOCATION: (601)..(840)
<223> OTHER INFORMATION: NOS terminator
<220> FEATURE:
<221> NAME/KEY: MISC_FEATURE
<222> LOCATION: (841)..(1980)
<223> OTHER INFORMATION: ACTII Promoter
<220> FEATURE:
<221> NAME/KEY: MISC_FEATURE
<222> LOCATION: (2101)..(2820)
<223> OTHER INFORMATION: NPT II Kan Resistance
<220> FEATURE:
<221> NAME/KEY: MISC_FEATURE
<222> LOCATION: (2941)..(3120)
<223> OTHER INFORMATION: NOS Terminator

<400> SEQUENCE: 31
```

| | | |
|---|---|---|
| aagcttccag aaggtaatta tccaagatgt agcatcaaga atccaatgtt tacgggaaaa | 60 |
| actatggaag tattatgtga gctcagcaag aagcagatca atatgcggca catatgcaac | 120 |
| ctatgttcaa aaatgaagaa tgtacagata caagatccta tactgccaga atacgaagaa | 180 |
| gaatacgtag aaattgaaaa agaagaacca ggcgaagaaa agaatcttga agacgtaagc | 240 |
| actgacgaca acaatgaaaa gaagaagata aggtcggtga ttgtgaaaga gacatagagg | 300 |
| acacatgtaa ggtggaaaat gtaagggcgg aaagtaacct tatcacaaag gaatcttatc | 360 |
| ccccactact tatcctttta tatttttccg tgtcattttt gcccttgagt tttcctatat | 420 |
| aaggaaccaa gttcggcatt tgtgaaaaca agaaaaaatt tggtgtaagc tattttcttt | 480 |
| gaagtactga ggatacaact tcagagaaat ttgtaagttt gtggatcctg caggctagcg | 540 |
| tgcactctag actcgacgaa ctgacgagct cgaatttccc cgatcgttca acatttggc | 600 |
| aataaagttt cttaagattg aatcctgttg ccggtcttgc gatgattatc atataatttc | 660 |
| tgttgaatta cgttaagcat gtaataatta acatgtaatg catgacgtta tttatgagat | 720 |
| gggtttttat gattagagtc ccgcaattat acatttaata cgcgatagaa aacaaaatat | 780 |
| agcgcgcaaa ctatgataaa ttatcgcgcg cggtgtcatc tatgttacta gatcgggaat | 840 |
| tcctcgagca actattttta tgtatgcaag agtcagcata tgtataattg attcagaatc | 900 |
| gttttgacga gttcggatgt agtagtagcc attatttaat gtacatacta atcgtgaata | 960 |
| gtgaatatga tgaaacattg tatcttattg tataaatatc cataaacaca tcatgaaaga | 1020 |
| cactttcttt cacggtctga attaattatg atacaattct aatagaaaac gaattaaatt | 1080 |
| acgttgaatt gtatgaaatc taattgaaca agccaaccac gacgacgact aacgttgcct | 1140 |
| ggattgactc ggtttaagtt aaccactaaa aaaacggagc tgtcatgtaa cacgcggatc | 1200 |
| gagcaggtca cagtcatgaa gccatcaaag caaaagaact aatccaaggg ctgagatgat | 1260 |
| taattagttt aaaaattagt taacacgagg gaaaaggctg tctgacagcc aggtcacgtt | 1320 |
| atctttacct gtggtcgaaa tgattcgtgt ctgtcgattt taattatttt tttgaaaggc | 1380 |
| cgaaaataaa gttgtaagag ataaacccgc ctatataaat tcatatattt tcctctccgc | 1440 |
| tttgaattgt ctcgttgtcc tcctcacttt catcagccgt tttgaatctc cggcgacttg | 1500 |
| acagagaaga acaaggaaga agactaagag agaaagtaag agataatcca ggagattcat | 1560 |
| tctccgtttt gaatcttcct caatctcatc ttcttccgct ctttctttcc aaggtaatag | 1620 |

```
gaactttctg atctactttt atttgctgga tctcgatctt gttttctcaa tttccttgag    1680
atctggaatt cgtttaattt ggatctgtga acctccacta aatcttttgg ttttactaga    1740
atcgatctaa gttgaccgat cagttagctc gattatagct accagaattt ggcttgacct    1800
tgatggagag atccatgttc atgttacctg gaaatgatt tgtatatgtg aattgaaatc      1860
tgaactgttg aagttagatt gaatctgaac actgtcaatg ttagattgaa tctgaacact    1920
gtttaaggtt agatgaagtt tgtgtataga ttcttcgaaa ctttaggatt tgtagtgtcg    1980
tacgttgaac agaaagctat ttctgattca atcagggttt atttgactgt attgaactct    2040
ttttgtgtgt ttgcagctca taaaaggtac caaacaatga ttgaacaaga tggattgcac    2100
gcaggttctc cggccgcttg ggtggagagg ctattcggct atgactgggc acaacagaca    2160
atcggctgct ctgatgccgc cgtgttccgg ctgtcagcgc aggggcgccc ggttcttttt    2220
gtcaagaccg acctgtccgg tgccctgaat gaactgcagg acgaggcagc gcggctatcg    2280
tggctggcca cgacgggcgt tccttgcgca gctgtgctcg acgttgtcac tgaagcggga    2340
agggactggc tgctattggg cgaagtgccg gggcaggatc tcctgtcatc tcaccttgct    2400
cctgccgaga agtatccat catggctgat gcaatgcggc ggctgcatac gcttgatccg    2460
gctacctgcc cattcgacca ccaagcgaaa catcgcatcg agcgagcacg tactcggatg    2520
gaagccggtc ttgtcgatca ggatgatctg gacgaagagc atcaggggct cgcgccagcc    2580
gaactgttcg ccaggctcaa ggcgcgcatg cccgacggcg aggatctcgt cgtgacccat    2640
ggcgatgcct gcttgccgaa tatcatggtg gaaaatggcc gcttttctgg attcatcgac    2700
tgtggccggc tgggtgtggc ggaccgctat caggacatag cgttggctac ccgtgatatt    2760
gctgaagagc ttggcggcga atgggctgac cgcttcctcg tgctttacgg tatcgccgct    2820
cccgattcgc agcgcatcgc cttctatcgc cttcttgacg agttcttttg agcgggactc    2880
tggcgatcgc cccgatcgtt caaacatttg gcaataaagt ttcttaagat tgaatcctgt    2940
tgccggtctt gcgatgatta tcatataatt tctgttgaat acgttaagc atgtaataat     3000
taacatgtaa tgcatgacgt tatttatgag atgggttttt atgattagag tcccgcaatt    3060
atacatttaa tacgcgatag aaaacaaaat atagcgcgca aactaggata aattatcgcg    3120
cgcggtgtca tctatgttac tagatcggga ctagt                               3155
```

<210> SEQ ID NO 32
<211> LENGTH: 20
<212> TYPE: PRT
<213> ORGANISM: Nicotiana tabacum

<400> SEQUENCE: 32

Asn Gly Gly Gly Lys Thr Thr Ser Leu Gly Lys Leu Ala Asn Arg Leu
1               5                   10                  15

Lys Lys Glu Gly
            20

<210> SEQ ID NO 33
<211> LENGTH: 23
<212> TYPE: PRT
<213> ORGANISM: Nicotiana tabacum

<400> SEQUENCE: 33

Arg Gly Gly Cys Val Val Ser Val Val Asp Glu Leu Gly Ile Pro Val
1               5                   10                  15

Lys Phe Val Gly Val Gly Glu
            20

```
<210> SEQ ID NO 34
<211> LENGTH: 20
<212> TYPE: PRT
<213> ORGANISM: Nicotiana tabacum

<400> SEQUENCE: 34

Lys Arg Gly Lys Gly Glu Asn Val Glu Tyr Leu Val Lys Trp Lys Asp
1               5                   10                  15

Gly Glu Asp Asn
            20

<210> SEQ ID NO 35
<211> LENGTH: 22
<212> TYPE: PRT
<213> ORGANISM: Nicotiana tabacum

<400> SEQUENCE: 35

Arg Thr Ala Leu Leu Phe Val Ser Gly Leu Gly Ser Glu Pro Cys Val
1               5                   10                  15

Lys Leu Leu Ala Glu Ala
            20

<210> SEQ ID NO 36
<211> LENGTH: 20
<212> TYPE: PRT
<213> ORGANISM: Nicotiana tabacum

<400> SEQUENCE: 36

Arg Arg Ser Glu Ser Arg Lys Gln Phe Ala Asp Ser Gly Ser Thr Arg
1               5                   10                  15

Pro Gly Pro Arg
            20

<210> SEQ ID NO 37
<211> LENGTH: 18
<212> TYPE: PRT
<213> ORGANISM: Nicotiana tabacum

<400> SEQUENCE: 37

Leu Lys Glu Val Lys Arg Val Leu Asn Pro Thr Glu Val Leu Leu Val
1               5                   10                  15

Val Asp

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atggcttctc tattatcttc tcgtctc                                              27

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
```
gttcaaatgc tcagctggtg aacg                                          25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgtcaattcc tctctctccc gcctc                                         25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cttcagaacc agcagcaaca agcag                                         25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atggaagcca ctgcttctttt ctcctc                                       26

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctcattcact agggatacat ggagggtg                                      28

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 44

His His His His His His
1               5

<210> SEQ ID NO 45
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
ggatccatgg cttctctatt atcttctcgt ctcccacgtc atctttcctc taataaaccg    60
gtactcccac catcaagctc cggttcaaat tccttcaca acttcacata taaaacccgg   120
ttcgatcaat cccggttcaa atgctcagct ggtggaacgg ggttcttcac gaagttgggt   180
cgtttgctga aagagaaagc aaagagcgac gtggagaaac tgttctcagg attctcaaaa   240
actcgagaca atttagcagt tatagatgaa ctcctccttt actgg                   285
```

<210> SEQ ID NO 46
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
taataagatc ttcaacacct acaccatttt tttaatcact actacccatt gcattgaaca    60
aacttccaag ttcttcttag cttcagatta agaaagtacc ctttcttggc tttgttgatg   120
tggtaccatt gtccattgtc ttgtgtgttt cca                                153
```

<210> SEQ ID NO 47
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
ccagtaaagg aggagttcat ctataactgc taaattgtct cgagttttg agaatcctga     60 gaacagtttc tccacgtcgc tctttgcttt ctctttcagc aaacgaccca acttcgtgaa   120
gaaccccgtt ccaccagctg agcatttgaa ccgggattga tcgaaccggg ttttatatgt   180
gaagttgtga aggagatttg aaccggagct tgatggtggg agtaccggtt tattagagga   240
aagatgacgt gggagacgag aagataatag agaagccatt ctaga                   285
```

<210> SEQ ID NO 48
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
ggatccggga aaggaatgga gtacttgata gagtggaaag acgaacatgc cccaacgtgg    60
gtcccctctg attacattgc taaagatgtt gtggccgagt acgaaactcc ttggtggaat   120
gcggctaaaa aggccgacga atccgctctt agggaactcc tagaaactga cgacgacaga   180
gatgtggacg cagtagatga ggatggacgt acggctttgc tctttgtctc gggtctgggg   240
tccgagccgt gtgtcaagct gctagctgaa gccggcgctg acgtggacta tcgcgatagg   300
aatggc                                                              306
```

<210> SEQ ID NO 49
<211> LENGTH: 153
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49
taataagatc ttcaacacct acaccatttt tttaatcact actacccatt gcattgaaca    60
aacttccaag ttcttcttag cttcagatta agaaagtacc ctttcttggc tttgttgatg    120
tggtaccatt gtccattgtc ttgtgtgttt cca    153

<210> SEQ ID NO 50
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gccattccta tcgcgatagt ccacgtcagc gccggcttca gctagcagct tgacacacgg    60
ctcggacccc agacccgaga caaagagcaa agccgtacgt ccatcctcat ctactgcgtc    120
cacatctctg tcgtcgtcag tttctaggag ttccctaaga gcggattcgt cggcctttt    180 agccgcattc caccaaggag tttcgtactc ggccacaaca tctttagcaa tgtaatcaga    240
ggggacccac gttgggcat gttcgtcttt ccactctatc aagtactcca ttcctttccc    300
tctaga    306

<210> SEQ ID NO 51
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
ggatccatgg aagccactgc ttctttctcc tcaactatgt cttcccacca tttctttcca    60
ctttccaaag ccaccctctc aacttctaaa cttccatttt ctgggactgg ttcaactcat    120
tctctttcat tttcttcaag aaactcattc actagggata catggagggt gatcaattca    180
aggaatgtgg ttatttcaag aagagaaatg cgtggagtta ttagagctga gatgtttgga    240
cagctcacta gtggacttga atcagcttgg aataagctca aggagaaga ggttttg    297

<210> SEQ ID NO 52
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
taataagatc ttcaacacct acaccatttt tttaatcact actacccatt gcattgaaca    60
aacttccaag ttcttcttag cttcagatta agaaagtacc ctttcttggc tttgttgatg    120
tggtaccatt gtccattgtc ttgtgtgttt cca    153

<210> SEQ ID NO 53
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
caaaacctct tctcctttga gcttattcca agctgattca agtccactag tgagctgtcc    60
aaacatctca gctctaataa ctccacgcat ttctcttctt gaaataacca cattccttga   120
attgatcacc ctccatgtat ccctagtgaa tgagtttctt gaagaaaatg aaagagaatg   180
agttgaacca gtcccagaaa atggaagttt agaagttgag agggtggctt tggaaagtgg   240
aaagaaatgg tgggaagaca tagttgagga gaaagaagca gtggcttcca ttctaga     297
```

<210> SEQ ID NO 54
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
ggatccgagg caggtgagtt aacaaacaag aaaagctcct ggttgacact ctttgatgtg    60
gaagatccaa ggtcaaaatt tcctcagtct aaaggcaagt tcctggatgc aaatcaagct   120
ttagaagttg ctagatttga tatacaatat tgtgattggc gagctcggca agatgtatta   180
accataatgc tcctgcacga aaaggttgtg aagtattga  atcctctggc acgtgagtac   240
aaatctattg gaaccatgaa aaaggaactt gcagagttgc aaggagagct ttctcaggcc   300
cacaaccagg tacatatatc tgaggcccgg gtttctgctg ctttggataa gctagcttac   360
atggaagagt tggttaatga taggcttctg caagagagaa gcacggcaga atcagat     417
```

<210> SEQ ID NO 55
<211> LENGTH: 153
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
taataagatc ttcaacacct acaccatttt tttaatcact actacccatt gcattgaaca    60
aacttccaag ttcttcttag cttcagatta agaaagtacc ctttcttggc tttgttgatg   120
tggtaccatt gtccattgtc ttgtgtgttt cca                                153
```

<210> SEQ ID NO 56
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
atctgattct gccgtgcttc tctcttgcag aagcctatca ttaaccaact cttccatgta    60
agctagctta tccaaagcag cagaaacccg ggcctcagat atatgtacct ggttgtgggc   120
ctgagaaagc tctccttgca actctgcaag ttccttttc atggttccaa tagatttgta   180
ctcacgtgcc agaggattca atacttccac aaccttttcg tgcaggagca ttatggttaa   240
tacatcttgc cgagctcgcc aatcacaata ttgtatatca aatctagcaa cttctaaagc   300
```

```
ttgatttgca tccaggaact tgcctttaga ctgaggaaat tttgaccttg gatcttccac    360
atcaaagagt gtcaaccagg agcttttctt gtttgttaac tcacctgcct ctctaga      417
```

TOBACCO PLANTS EXHIBITING ALTERED PHOTOSYNTHESIS AND METHODS OF MAKING AND USING

CROSS REFERENCE TO RELATED APPLICATIONS

This application is a continuation of U.S. application Ser. No. 16/579,271, filed Sep. 23, 2019 (now U.S. Pat. No. 11,174,490), which is a continuation of U.S. application Ser. No. 15/486,841, filed Apr. 13, 2017 now U.S. Pat. No. 10,457,953), which claims the benefit of priority under 35 U.S.C. § 119(e) to U.S. Provisional Application 62/322,001, filed Apr. 13, 2016, which are incorporated herein by reference in their entireties.

INCORPORATION OF SEQUENCE LISTING

The file named P34456US04 SL.txt contains the Sequence Listing that was created on Nov. 3, 2021. This file is 67,861 bytes (measured in MS Windows), is contemporaneously filed by electronic submission (using the United States Patent Office EFS-Web filing system), and is incorporated herein by reference in its entirety.

TECHNICAL FIELD

This disclosure generally relates to plants that exhibit altered photosynthesis.

BACKGROUND

During photosynthesis, at low sunlight intensities, all absorbed photons are utilized efficiently to drive electrons in the electron-transport chain. As the level of irradiance increases further, photosynthesis becomes saturated and reaches a plateau due to the fact that the carbon reactions cannot keep up with the linear increase in light absorption. Plant lines with a wild type light-harvesting antenna system reach this light intensity for saturation at lower levels of irradiance than their mutant counterparts. The sunlight harvested by the chlorophyll antenna exceeds the maximal operational capacity of the electron-transport chain and of the carbon reactions of photosynthesis, rendering the excess absorbed photons useless. Under bright sunlight conditions (2500 µmol photons m-2 s-1), wild type lines with their fully developed light-harvesting antenna utilize photons inefficiently; only about 20% of the incoming sunlight energy is converted into useful photosynthesis, while excess absorbed energy is dissipated by the non-photochemical quenching (NPQ) process.

SUMMARY

Tobacco plants that exhibit altered photosynthesis are provided herein, as well as methods of making and using such plants.

In one aspect, a method of making a *Nicotiana tabacum* plant is provided. Such a method typically includes inducing mutagenesis in *N. tabacum* cells to produce mutagenized *N. tabacum* cells; obtaining one or more *N. tabacum* plants from the mutagenized *N. tabacum* cells; and identifying at least one of the *N. tabacum* plants that comprises a mutated TLA or CAO sequence. Representative TLA or CAO sequences have at least 95% sequence identity to a sequence shown in SEQ ID NO: 11, 13, 15, 17, 19, 21, 23 or 25.

Such a method further can include identifying at least one of the *N. tabacum* plants that exhibits reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass relative to a *N. tabacum* plant lacking a mutated TLA or CAO sequence.

In some embodiments, leaf from the mutant *N. tabacum* plant exhibits comparable or better quality than leaf from the plant lacking a mutated TLA or CAO sequence. In some embodiments, the *N. tabacum* plant is a Burley type, a dark type, a flue-cured type, or an Oriental type.

In another aspect, a variety of *Nicotiana tabacum* is provided. Such a variety typically includes plants having a mutation in an endogenous nucleic acid, where the wild type endogenous nucleic acid encodes the TLA or CAO sequence shown in SEQ ID NO:12, 14, 16, 18, 20, 22, 24 or 26. Typically, leaf from the mutant plants exhibits reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass relative to leaf from a plant lacking the mutation. In some embodiments, leaf from the mutant *N. tabacum* plant exhibits comparable or better quality than leaf from the plant lacking a mutated TLA sequence.

In another aspect, cured leaf from one of the *N. tabacum* varieties described herein is provided. In still another aspect, a tobacco product that includes such cured leaf is provided. Representative tobacco products include, without limitation, cigarettes, smokeless tobacco products, tobacco-derived nicotine products, cigarillos, non-ventilated recess filter cigarettes, vented recess filter cigarettes, cigars, snuff, electronic cigarettes, e-vapor products, pipe tobacco, cigar tobacco, cigarette tobacco, chewing tobacco, leaf tobacco, shredded tobacco, and cut tobacco.

In still another aspect, a RNA nucleic acid molecule is provided. Such a RNA nucleic acid molecule typically includes a first nucleic acid between 15 and 500 nucleotides in length and a second nucleic acid between 15 and 500 nucleotides in length, where the first nucleic acid has a region of complementarity to the second nucleic acid, and where the first nucleic acid comprises at least 15 contiguous nucleotides of the sequence shown in SEQ ID NO: 11, 13, 15, 17, 19, 21, 23 or 25. In some embodiments, the RNA nucleic acid molecule further includes a spacer nucleic acid between the first nucleic acid and the second nucleic acid.

In one aspect, a method of making a *Nicotiana tabacum* plant is provided. Such a method typically includes transforming *N. tabacum* cells with the nucleic acid molecule of claim 12 to produce transgenic *N. tabacum* cells; regenerating transgenic *N. tabacum* plants from the transgenic *N. tabacum* cells; and selecting at least one transgenic *N. tabacum* plant that comprises the nucleic acid molecule or the construct. In some embodiments, such a method further includes identifying at least one transgenic *N. tabacum* plant having reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass relative to a *N. tabacum* plant not transformed with the nucleic acid molecule. In some embodiments, leaf from the selected transgenic *N. tabacum* plant exhibits comparable or better quality than leaf from the non-transformed *N. tabacum* plant.

In another aspect, a transgenic *Nicotiana tabacum* plant is provided that includes a vector, where the vector includes a RNA nucleic acid molecule having a length of 15 to 500 nucleotides and has at least 95% sequence identity to a TLA or CAO nucleic acid shown in SEQ ID NO: 11, 13, 15, 17, 19, 21, 23 or 25. In some embodiments, leaf from the plant exhibits comparable or better quality than leaf from a *N. tabacum* plant lacking the nucleic acid molecule.

In one aspect, cured leaf from such transgenic *N. tabacum* plants is provided. In one aspect, tobacco products that include such cured leaf are provided. Representative tobacco products include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1A:
FIG. 1A is a photograph of a wild type tobacco plant (left) and a T0 tobacco plant transgenic for a RNAi nucleic acid molecule directed toward TLA2 (TLA2i-1; right).

Photosynthetic organisms (e.g., green plants, algae, and many bacteria) contain reaction centers, which is a complex of proteins, pigments and co-factors that perform the photosynthetic conversion of light to energy via a multitude of electron transfer steps. Despite the evolutionary distances between such photosynthetic organisms, the reaction centers possess remarkable homology. In contrast, the light-harvesting complexes in the various photosynthetic organisms differ. The current methods used to measure light absorption and utilization in plants and microalgae are described in Melis and Thielen (1980, *Biochim. Biophys. Acta,* 589:275-86) and Melis (1989, *Philos. Trans. R. Soc. Lond. B,* 323:397-409).

During the process of photosynthesis, the light-harvesting complex, which typically surrounds the reaction center, absorbs the light (e.g., sunlight). In plants, the light energy is absorbed by the light-harvesting antenna complex and is transferred to two chlorophyll a molecules, which are embedded in the reaction center. As described herein, light-harvesting antenna complex size can be inhibited or reduced in tobacco using, for example, mutagenesis or RNAi, to diminish over-absorption of sunlight at the higher canopy. Diminishing over-absorption of sunlight in the higher canopy of the plant can minimize wasteful dissipation of energy, while, at the same time, allowing for a far greater transmittance of sunlight deeper into the lower canopy by eliminating unwanted shading, particularly under high density growth conditions.

Tobacco genes and the encoded proteins were screened to identify those involved in harvesting light; those sequences identified in the screen were evaluated further to identify their mode of action. The sequences identified herein can be inhibited (e.g., by RNA interference and/or mutation) to result in smaller light-harvesting chlorophyll antenna size, which ultimately results in a plant that exhibits substantially improved photosynthetic efficiency. A number of tobacco sequences (e.g., truncated light-harvesting antenna (TLA) 2, TLA3, TLA4 and CAO (Chlorophyllide a oxygenase)) as well as corresponding homologues from *Chlamydomonas* and/or *Arabidopsis* were obtained.

Four TLA-related genes, TLA2 and TLA2 Homo (encoding the CpFTSY protein), TLA3 and TLA3 Homo (encoding the CpSRP43 protein), and TLA4 (encoding the CpSRP54 protein) were obtained from *Nicotiana tabacum*, as well as three CAO genes (CAO-2, COA-3 and CAO-4). Based on sequence alignment, CAO-2 appears to have originated from *Nicotiana tometosiformis*, while both CAO-3 and COA-4 originated from *Nicotiana sylvestris*.

As described in more detail below, the expression of one or more of the sequences described herein can be inhibited or reduced using, for example, mutagenesis or inhibitory RNA (RNAi). The resulting plants can be evaluated for total chlorophyll, as well as the ratio of chlorophyll a:chlorophyll b and/or the photosynthetic apparatus size in Photosystem I (PSI) and/or Photosystem II (PSII). Sequences that, when their expression is knocked down or completely eliminated, result in a higher ratio of chlorophyll a:b and reduced antenna size in PSI and/or PSII systems were desired, as it is these sequences that will substantially improve photosynthetic efficiency.

As described herein, modification of TLA sequences and CAO sequences in tobacco results in smaller light-harvesting chlorophyll antenna complex size by reducing antenna number and a substantially improved photosynthetic efficiency. The modified tobacco lines further exhibit enhanced productivity (e.g., increased biomass).

Specifically, for example, knocking down TLA2 resulted in plants that grow slower than wild type plants, plants that have a ratio of Chlorophyll a:Chlorophyll b similar to wild type, plants that have an antenna size in PSI that is similar to wild type, plants that have an antenna size in PSII that is reduced compared to wild type plants, and plants that have a lighter leaf color than wild type plants due to the reduction of total chlorophyll content.

In addition, knocking down TLA3 resulted in plants that grow at a similar rate to wild type plants, plants that have a ratio of Chlorophyll a:Chlorophyll b that is increased relative to wild type plants, plants that have an antenna size in both PSI and PSII that is reduced compared to wild type plants, plants in which the amount of total chlorophyll increased from low to normal levels during maturation, relative to wild type plants.

Further, knocking down TLA4 resulted in plants in which the amount of total chlorophyll was reduced, but both the ratio of chlorophyll a:chlorophyll b and the antenna size in both PSI and PSII were unchanged.

Light Harvesting Antenna Nucleic Acids and Polypeptides

Nucleic acids encoding TLA2, TLA2-homo, TLA3, TLA3-homo and TLA4 from *N. tabacum* are shown in SEQ ID NOs: 11, 13, 15, 17, and 19, respectively, and nucleic acids encoding CAO2, CAO3 and CAO4 from *N. tabacum* are shown in SEQ ID NOs: 21, 23, and 25, respectively. Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

The sequence of the TLA2, TLA2-homo, TLA3, TLA3-homo and TLA4 polypeptides from *N. tabacum* are shown in SEQ ID NOs: 12, 14, 16, 18, and 20, respectively, and the sequences of the CAO2, CAO3 and CAO4 polypeptides from *N. tabacum* are shown in SEQ ID NOs: 22, 24, and 26, respectively. As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Nucleic acids can be detected using any number of amplification techniques (see, e.g., *PCR Primer: A Laboratory Manual*, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization.

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is oftentimes accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

A construct, sometimes referred to as a vector, containing a nucleic acid (e.g., a coding sequence or a RNAi nucleic acid molecule) is provided. Constructs, including expression constructs (or expression vectors), are commercially available or can be produced by recombinant DNA techniques routine in the art. A construct containing a nucleic acid can have expression elements operably linked to such a nucleic acid, and further can include sequences such as those encoding a selectable marker (e.g., an antibiotic resistance gene). A construct can encode a chimeric or fusion polypeptide (i.e., a first polypeptide operatively linked to a second polypeptide). Representative first (or second) polypeptides are those that can be used in purification of the other (i.e., second (or first), respectively) polypeptide including, without limitation, 6× His (SEQ ID NO:44) tag or glutathione S-transferase (GST).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s)

are positioned in a vector relative to a nucleic acid in such a way as to direct or regulate expression of the nucleic acid (e.g., in-frame).

Constructs as described herein can be introduced into a host cell. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer. As used herein, "host cell" refers to the particular cell into which the nucleic acid is introduced and also includes the progeny or potential progeny of such a cell. A host cell can be any prokaryotic or eukaryotic cell. For example, nucleic acids can be introduced into bacterial cells such as E. coli, or into insect cells, yeast or mammalian cells (such as Chinese hamster ovary cells (CHO) or COS cells). Other suitable host cells are known to those skilled in the art.

RNA Interfering Nucleic Acids and Constructs Containing Same

RNA interference (RNAi), also called post-transcriptional gene silencing (PTGS), is a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). In transgenic plants, the use of RNAi can involve the introduction of long dsRNA (e.g., greater than 50 bps) or siRNAs (e.g., 12 to 23 bps) that have complementarity to the target gene, both of which are processed by the endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery.

A RNAi nucleic acid molecule as described herein is complementary to at least a portion of a target mRNA (e.g., a TLA mRNA, a CAO mRNA), and typically is referred to as an "antisense strand". Typically, the antisense strand includes at least 15 contiguous nucleotides of the DNA sequence (e.g., the nucleic acid sequence shown in SEQ ID NO:11, 13, 15, 17, 19, 21, 23, or 25); it would be appreciated that the antisense strand has the "RNA equivalent" sequence of the DNA (e.g., uracils instead of thymines; ribose sugars instead of deoxyribose sugars).

A RNAi nucleic acid molecule can be, for example, 15 to 500 nucleotides in length (e.g., 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, the anti sense strand (e.g., a first nucleic acid) can be accompanied by a "sense strand" (e.g., a second nucleic acid), which is complementary to the antisense strand. In the latter case, each nucleic acid (e.g., each of the sense and antisense strands) can be between 15 and 500 nucleotides in length (e.g., between 15 to 50, 15 to 45, 15 to 30, 16 to 47, 16 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 15 to 100, 15 to 300, 15 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, a spacer nucleic acid, sometimes referred to as a loop nucleic acid, can be positioned between the sense strand and the antisense strand. In some embodiments, the spacer nucleic acid can be an intron (see, for example, Wesley et al., 2001, *The Plant J.,* 27:581-90). In some embodiments, although not required, the intron can be functional (i.e., in sense orientation; i.e., spliceable) (see, for example, Smith et al., 2000, *Nature,* 407:319-20). A spacer nucleic acid can be between 20 nucleotides and 1000 nucleotides in length (e.g., 25-800, 25-600, 25-400, 50-750, 50-500, 50-250, 100-700, 100-500, 100-300, 250-700, 300-600, 400-700, 500-800, 600-850, or 700-1000 nucleotides in length).

In some embodiments, a construct can be produced by operably linking a promoter that is operable in plant cells; a DNA region, that, when transcribed, produces an RNA molecule capable of forming a hairpin structure; and a DNA region involved in transcription termination and polyadenylation. It would be appreciated that the hairpin structure has two annealing RNA sequences, where one of the annealing RNA sequences of the hairpin RNA structure includes a sense sequence identical to at least 20 consecutive nucleotides of a TLA or CAO nucleotide sequence, and where the second of the annealing RNA sequences includes an antisense sequence that is identical to at least 20 consecutive nucleotides of the complement of the TLA or CAO nucleotide sequence. In addition, as indicated herein, the DNA region can include an intron (e.g., a functional intron). When present, the intron generally is located between the two annealing RNA sequences in sense orientation such that it is spliced out by the cellular machinery (e.g., the splicesome). Such a construct can be introduced into one or more plant cells to reduce the phenotypic expression of a nucleic acid (e.g., a nucleic acid sequence that is normally expressed in a plant cell).

In some embodiments, a construct (e.g., an expression construct) can include an inverted-duplication of a segment of a TLA or CAO gene, where the inverted-duplication of the TLA or CAO gene segment includes a nucleotide sequence substantially identical to at least a portion of the TLA or CAO gene and the complement of the portion of the TLA or CAO gene, respectively. It would be appreciated that a single promoter can be used to drive expression of the inverted-duplication of the TLA or CAO gene segment, and that the inverted-duplication typically contains at least one copy of the portion of the TLA or CAO gene in the sense orientation. Such a construct can be introduced into one or more plant cells to delay, inhibit or otherwise reduce the expression of a TLA or CAO gene in the plant cells.

Representative RNAi nucleic acid molecules directed toward TLA2, TLA3 and TLA4 are shown in SEQ ID NOs: 27, 28 and 29, respectively, and a representative RNAi nucleic acid molecule directed toward CAO2, CAO3 and CAO4 is shown in SEQ ID NO:30. The sense strand and antisense strand are identified with dashed underlining, and a spacer or loop sequence lies between. It would be appreciated by the skilled artisan that the region of complementarity, between the antisense strand of the RNAi and the mRNA or between the antisense strand of the RNAi and the sense strand of the RNAi, can be over the entire length of the RNAi nucleic acid molecule, or the region of complementarity can be less than the entire length of the RNAi nucleic acid molecule. For example, a region of complementarity can refer to, for example, at least 15 nucleotides in length up to, for example, 500 nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 nucleotides in length). In some embodiments, a region of complementarity can refer to, for example, at least 15 contiguous nucleotides in length up to, for example, 500 contiguous nucleotides in length (e.g., at least 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 contiguous nucleotides in length).

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides (or amino acid residues) between the two nucleic acids (or polypeptides) is determined. The number of identical matches is divided by the length of the aligned region (i.e., the number of aligned nucleotides (or amino acid residues)) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid or polypeptide sequences to be carried out across their entire length (global alignment). Chenna et al., 2003, *Nucleic Acids Res.*, 31(13):3497-500. ClustalW calculates the best match between a query and one or more subject sequences (nucleic acid or polypeptide), and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, *Molecular Cloning: A Laboratory Manual*, 2nd Ed., Cold Spring Harbor Laboratory Press, Cold Spring Harbor, NY; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, CA).

A construct (also known as a vector) containing a RNAi nucleic acid molecule is provided. Constructs, including expression constructs, are described herein and are known to those of skill in the art. Expression elements (e.g., promoters) that can be used to drive expression of a RNAi nucleic acid molecule are known in the art and include, without limitation, constitutive promoters such as, without limitation, the cassava mosaic virus (CsMVM) promoter, the cauliflower mosaic virus (CaMV) 35S promoter, the actin promoter, or the glyceraldehyde-3-phosphate dehydrogenase promoter, or tissue-specific promoters such as, without limitation, root-specific promoters such as the putrescine N-methyl transferase (PMT) promoter or the quinolinate phosphosibosyltransferase (QPT) promoter. It would be understood by a skilled artisan that a sense strand and an antisense strand can be delivered to and expressed in a target cell on separate constructs, or the sense and antisense strands can be delivered to and expressed in a target cell on a single construct (e.g., in one transcript). As discussed herein, a RNAi nucleic acid molecule delivered and expressed on a single strand also can include a spacer nucleic acid (e.g., a loop nucleic acid) such that the RNAi forms a small hairpin (shRNA).

Transgenic Plants and Methods of Making Transgenic Plants

Transgenic N. tabacum plants are provided that contain a transgene encoding at least one RNAi molecule, which, when transcribed, silences expression of any of the TLA or CAO sequences described herein. As used herein, silencing can refer to complete elimination or essentially complete elimination of the TLA or CAO mRNA, resulting in 100% or essentially 100% reduction (e.g., greater than 95% reduction; e.g., greater than 96%, 97%, 98% or 99% reduction) in the amount of encoded TLA or CAO polypeptide; silencing also can refer to partial elimination of the TLA or CAO mRNA (e.g., eliminating about 5%, 10%, 15%, 20%, 25%, 30%, 35%, 40%, 45%, 50% or more of the TLA or CAO mRNA), resulting in a reduction (e.g., about 5%, 10%, 15%, 20%, 25%, 30%, 35%, 40%, 45%, 50% or more, but not complete elimination) in the amount of the encoded TLA or CAO polypeptide.

A RNAi nucleic acid molecule can be transcribed using a plant expression vector. Methods of introducing a nucleic acid (e.g., a heterologous nucleic acid) into plant cells (e.g., N. tabacum cells) are known in the art and include, for example, particle bombardment, Agrobacterium-mediated transformation, microinjection, polyethylene glycol-mediated transformation (e.g., of protoplasts, see, for example, Yoo et al. (2007, Nature Protocols, 2(7):1565-72)), liposome-mediated DNA uptake, or electroporation.

Following transformation, the transgenic plant cells can be regenerated into transgenic tobacco plants. The regenerated transgenic plants can be screened for the presence of the transgene (e.g., a RNAi nucleic acid molecule) and/or one or more of the resulting phenotypes (e.g., reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass).

Methods of detecting alkaloids (e.g., nicotine) or TSNAs, and methods of determining the amount of one or more alkaloids or TSNAs are known in the art. For example, high performance liquid chromatography (HPLC)—mass spectroscopy (MS) (HPLC-MS) or high performance thin layer chromatography (HPTLC) can be used to detect the presence of one or more alkaloids and/or determine the amount of one or more alkaloids. In addition, any number of chromatography methods (e.g., gas chromatography/thermal energy analysis (GC/TEA), liquid chromatography/mass spectrometry (LC/MS), and ion chromatography (IC)) can be used to detect the presence of one or more TSNAs and/or determine the amount of one or more TSNAs.

As used herein, "reduced" or "reduction" refers to a decrease (e.g., a statistically significant decrease), in green leaf or cured leaf, of/in one or more of the following: a) the amount of TLA or CAO mRNA; b) the amount of TLA or CAO polypeptide; c) the activity of a TLA or CAO polypeptide; d) the concentration of thylakoid membranes in the photosystems measured spectrophotometrically from the amplitude of the light-minus-dark absorbance difference signal at 800 nm (P800) for PSI and 320 nm (QA) for PSII (see, for example, Melis & Brown, 1980, PNAS USA, 77(8):4712-6; and Melis, 1989, Philos. Trans. R. Soc. Lord. B, 323:397-409); and/or e) the amount of total chlorophyll. As used herein, "reduced" or "reduction" refers to a decrease in any of the above by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

As used herein, "increased" refers to an increase (e.g., a statistically significant increase), in green leaf or cured leaf, of the ratio of chlorophyll a/chlorophyll b or in plant biomass. As used herein, "increased" refers to an increase in any of the above by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

Leaf from progeny plants also can be screened for the presence of the transgene and/or the resulting phenotype, and plants exhibiting the desired phenotype can be selected. As described herein, leaf from such transgenic plants can exhibit reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass in the plant (e.g., compared to leaf from a plant lacking or not transcribing the RNAi). Leaf from regenerated transgenic plants can be screened (e.g., reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass), and the desired plants (e.g., having leaf that exhibit reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass), compared to the amount in a leaf from a corresponding non-transgenic plant, can be selected and, for example, used in a breeding program.

Transgenic plants exhibiting the desired phenotype can be used, for example, in a breeding program. Breeding is carried out using known procedures. Successful crosses yield $F_1$ plants that are fertile and that can be backcrossed with one of the parents if desired. In some embodiments, a plant population in the $F_2$ generation is screened for the presence of a transgene and/or the resulting phenotype using standard methods (e.g., amplification, hybridization and/or chemical analysis of the leaf). Selected plants are then crossed with one of the parents and the first backcross ($BC_1$) generation plants are self-pollinated to produce a $BC_1F_2$ population that is again screened. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the transgene and exhibits variant gene expression. Breeder's seed of the selected plant can be produced using standard methods including, for example, field testing and/or chemical analyses of leaf (e.g., cured leaf).

The result of a plant breeding program using the transgenic tobacco plants described herein are novel and useful varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility where a transgene inhibits microsporogenesis and/or pollen formation, or self-incompatibility. Female parent plants having CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The tobacco plants used in the methods described herein can include, but are not limited to, a Burley type, a dark type, a flue-cured type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, Perique tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

Mutant Plants and Methods of Making

Methods of making a *N. tabacum* plant having a mutation are known in the art. Mutations can be random mutations or targeted mutations. For random mutagenesis, cells (e.g., *N. tabacum* cells) typically are mutagenized using, for example, a chemical mutagen or ionizing radiation. Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, *Nucleic Acids Res.*, 39(14):6315-25) or zinc-finger (see, for example, Wright et al., 2005, *The Plant J.*, 44:693-705). Whether random or targeted, a mutation can be a point mutation, an insertion, a deletion, a substitution, or combinations thereof, which are discussed in more detail below.

The resultant variety of *Nicotiana tabacum* includes plants having a mutation in an endogenous TLA nucleic acid (e.g., SEQ ID NOs: 11, 13, 15, 17 or 19) encoding a TLA polypeptide sequence (e.g., SEQ ID NOs: 12, 14, 16, 18 or 20) or in an endogenous CAO gene (e.g., SEQ ID NOs: 21, 23 or 25) encoding a CAO polypeptide sequence (e.g., SEQ ID NOs: 22, 24 or 26). A mutation in a TLA or CAO sequence as described herein typically results in reduced expression or activity of TLA or CAO, which, in turn, results in one or more of the phenotypes described herein (e.g., reduced concentration of thylakoid membranes in the photosystems; reduced amount of total chlorophyll; increased ratio of chlorophyll a to chlorophyll b; and/or increased biomass), or combinations thereof depending on the particular combination of sequences that are mutated or otherwise knocked-down, in the leaf of a mutant plant relative to a plant lacking the mutation.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Suitable types of mutations in a TLA or CAO coding sequence include, without limitation, insertions of nucleotides, deletions of nucleotides, or transitions or transversions relative to the wild-type TLA or CAO coding sequence, respectively. Mutations in the coding sequence can result in insertions of one or more amino acids, deletions of one or more amino acids, conservative or non-conservative amino acid substitutions in the encoded polypeptide, or truncation of the protein (e.g., by introduction of a stop codon). In some cases, the coding sequence of a TLA comprises more than one mutation and/or more than one type of mutation.

Insertion or deletion of amino acids in a coding sequence, for example, can disrupt the conformation of the encoded polypeptide. Amino acid insertions or deletions also can disrupt sites important for recognition of binding ligand(s) or substrate(s) or for activity of the polypeptide. It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the TLA or CAO polypeptide, introduce a stop codon to produce a truncated polypeptide, or disrupt an active site or domain (e.g., a catalytic site or domain, a binding site or domain) within the polypeptide.

A "conservative amino acid substitution" is one in which one amino acid residue is replaced with a different amino acid residue having a similar side chain (see, for example, Dayhoff et al. (1978, in *Atlas of Protein Sequence and Structure*, 5(Suppl. 3):345-352), which provides frequency tables for amino acid substitutions), and a non-conservative substitution is one in which an amino acid residue is replaced with an amino acid residue that does not have a similar side chain. Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Following mutagenesis, $M_0$ plants are regenerated from the mutagenized cells and those plants, or a subsequent generation of that population (e.g., $M_1$, $M_2$, $M_3$, etc.), can be screened for those carrying a mutation in a TLA of CAO sequence. Screening for plants carrying a mutation in a TLA of CAO nucleic acid or polypeptide can be performed directly using methods routine in the art (e.g., hybridization, amplification, nucleic acid sequencing, peptide sequencing, combinations thereof) or by evaluating the phenotype (e.g., reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass). It would be understood that the phenotype of a mutant plant (e.g., reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass) would be compared to a corresponding plant (e.g., having the same varietal background) that lacks the mutation.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype (e.g., reduced amount of TLA or CAO mRNA; reduced amount of TLA or CAO polypeptide; reduced activity of a TLA or CAO polypeptide; reduced concentration of thylakoid membranes in the photosystems; reduced amount of total chlorophyll; increased ratio of chlorophyll a to chlorophyll b; and/or increased biomass). Such plants may be heterozygous and exhibit a mutant phenotype due to a phenomenon such as dominant negative suppression, despite the presence of the wild type allele, or such plants may be homozygous due to independently induced mutations in both alleles.

As used herein, "reduced" or "reduction" refers to a decrease (e.g., a statistically significant decrease), in green leaf or cured leaf, of/in one or more of the following: a) the amount of TLA or CAO mRNA; b) the amount of TLA or CAO polypeptide; c) the activity of a TLA or CAO polypeptide; d) the concentration of thylakoid membranes in the photosystems measured spectrophotometrically from the amplitude of the light-minus-dark absorbance difference signal at 800 nm (P800) for PSI and 320 nm (QA) for PSII (see, for example, Melis & Brown, 1980, *PNAS USA*, 77(8):4712-6; and Melis, 1989, *Philos. Trans. R. Soc. Lond. B*, 323:397-409); and/or e) the amount of total chlorophyll. As used herein, "reduced" or "reduction" refers to a decrease in any of the above by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

As used herein, "increased" refers to an increase (e.g., a statistically significant increase), in green leaf or cured leaf, of the ratio of chlorophyll a/chlorophyll b or in plant biomass. As used herein, "increased" refers to an increase in any of the above by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the transgene. As used herein, statistical significance refers to a p-value of less than 0.05, e.g., a p-value of less than 0.025 or a p-value of less than 0.01, using an appropriate measure of statistical significance, e.g., a one-tailed two sample t-test.

A tobacco plant carrying a mutant allele can be used in a plant breeding program to create novel and useful lines, varieties and hybrids. Desired plants that possess the mutation can be backcrossed or self-pollinated to create a second population to be screened. Backcrossing or other breeding procedures can be repeated until the desired phenotype of the recurrent parent is recovered. DNA fingerprinting, SNP or similar technologies may be used in a marker-assisted selection (MAS) breeding program to transfer or breed mutant alleles into other tobaccos, as described herein.

In some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21) number of leaves).

Cured Tobacco and Tobacco Products

The methods described herein allow for increasing tobacco biomass while still maintaining high leaf quality. As described herein, such methods can include the production of transgenic (using, e.g., RNAi or overexpression) or mutant (e.g., random or targeted) plants.

Leaf quality can be determined, for example, using an Official Standard Grade published by the Agricultural Marketing Service of the US Department of Agriculture (7 U.S.C. § 511); Legacy Tobacco Document Library (Bates Document #523267826/7833, Jul. 1, 1988, Memorandum on the Proposed Burley Tobacco Grade Index); and Miller et al., 1990, *Tobacco Intern.*, 192:55-7. For dark-fired tobacco, leaves typically are obtained from stalk position C, and the average grade index determined based on Federal Grade and 2004 Price Support for Type 23 Western dark-fired tobacco.

Leaf from the tobacco described herein can be cured, aged, conditioned, and/or fermented. Methods of curing tobacco are well known and include, for example, air curing, fire curing, flue curing and sun curing. Aging also is known and is typically carried out in a wooden drum (e.g., a hogshead) or cardboard cartons in compressed conditions for several years (e.g., 2 to 5 years), at a moisture content of from about 10% to about 25% (see, for example, U.S. Pat. Nos. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993; 4,660,577; 4,848,373; and 5,372,149. The tobacco also can be further processed (e.g., cut, expanded, blended, milled or comminuted), if desired, and used in a tobacco product.

Tobacco products are known in the art and include any product made or derived from tobacco that is intended for human consumption, including any component, part, or accessory of a tobacco product. Representative tobacco products include, without limitation, cigarettes, smokeless tobacco products, tobacco-derived nicotine products, cigarillos, non-ventilated recess filter cigarettes, vented recess filter cigarettes, cigars, snuff, electronic cigarettes, e-vapor products, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, sticks, rods, and the like. Representative cigarettes and other smoking articles include, for example, smoking articles that include filter elements or rod elements, where the rod element of a smokeable material can include cured tobacco within a tobacco blend. In addition to the reduced-nicotine or reduced-TSNA tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Sampling, RNA Preparation and Sequencing

Tobacco leaf sample from a burley variety, TN90, was collected. RNA from the sample was isolated using RNeasy Plant Mini Kit (Qiagen; MA) and its quality tested using Agilent Plant RNA Nano Kit and a 2100 Bioanalyzer (Agilent Technologies, CA, USA). A cDNA library was constructed and indexed using a TrueSeq RNA Library Prep Kit v.2 (Illumina). cDNAs were run on an Illumina HiSeq 2000 under conditions for 100 bp single reads and a minimum of 30 million reads per sample. Leaf gene expression in TN90 tobacco was determined by RNA deep sequencing performed by ArrayXpress (Raleigh, NC).

Example 2—Tobacco TLA2, TLA3 and TLA4 Homologous Gene Identification, Full Length Gene Cloning TLA2, TLA3 and TLA4 gene sequences from *Chlamydomonas* and *Arabidopsis* were used to Blast the TN90 burley genomic sequence data base and leaf RNA sequence data. Five candidate genes were identified: TLA2, TLA2 Homo, TLA3, TLA3 Homo, and TLA4, and primers were designed to clone the five candidate genes. Leaf tissue was collected and a cDNA library was created using the In-Fusion® SMARTer® Directional cDNA Library Construction Kit from Clontech. Full length candidate genes were amplified using the gene specific primers designed from predicted full length cDNA sequences. The full length coding sequences were identified, cloned and confirmed by sequencing.

TABLE 1

Primers for TLA gene cloning

| Designation | SEQUENCE (5' to 3') | SEQ ID NO |
|---|---|---|
| TLA-2-F | ATGGCTTCTCTATTATCTTCTCGTC | 1 |
| TLA-2-R | TCATGGGAAGATAGCATTAACAAA | 2 |
| TLA-2-Homo-F | ATGGCTTCTCTATTATCTTCTCGTCTCC | 3 |

TABLE 1-continued

Primers for TLA gene cloning

| Designation | SEQUENCE (5' to 3') | SEQ ID NO |
|---|---|---|
| TLA-2-Homo-R | TTAAATAGAATCTGCCACATAAATG | 4 |
| TLA-3-F | ATGGATGCTCTCTTCGTCAATTCCTC | 5 |
| TLA-3-R | GCCCTTGTTCAACTTACTACATT | 6 |
| TLA-3-Homo-F | ATGGATGCTCTGTTCGTCAATTCCT | 7 |
| TLA-3-Homo-R | TCAACTTACTACATTCTGTTGACCC | 8 |
| TLA-4-F | ATGGAAGCCACTGCTTCTTTCTCCTCA | 9 |
| TLA-4-R | TTAGTTCTTGGCCCCAAAACCACGAG | 10 |

The sequence of the candidate genes are provided as indicated in Table 2.

TABLE 2

Candidate genes

| Gene name | Nucleic Acid | Polypeptide |
|---|---|---|
| TLA2 | SEQ ID NO: 11 | SEQ ID NO: 12 |
| TLA2-Homo | SEQ ID NO: 13 | SEQ ID NO: 14 |
| TLA3 | SEQ ID NO: 15 | SEQ ID NO: 16 |
| TLA3-homo | SEQ ID NO: 17 | SEQ ID NO: 18 |
| TLA4 | SEQ ID NO: 19 | SEQ ID NO: 20 |
| CAO-2 | SEQ ID NO: 21 | SEQ ID NO: 22 |
| CAO-3 | SEQ ID NO: 23 | SEQ ID NO: 24 |
| CAO-4 | SEQ ID NO: 25 | SEQ ID NO: 26 |

Example 3—RNAi Plasmid Construction and *Agrobacterium* Transformation

In order to investigate the function of the candidate genes, RNAi constructs were produced against TLA2, TLA3 and TLA4, and transgenic plant lines were generated. An *Agrobacterium* expression vector (SEQ ID NO:31) was used, which has a CsVMV promoter and a NOS terminator, as well as a cassette having a kanamycin selection marker (NPT II) under direction of the actin2 promoter and a NOS terminator. The nucleic acid constructs carrying each RNAi construct were introduced into tobacco leaf disc using an *Agrobacterium* transformation approach. See, for example, Mayo et al., 2006, *Nat Protoc.*, 1(3):1105-11, and Horsch et al., 1985, *Science*, 227:1229-31.

Briefly, ascetical tobacco plants (Narrow Leaf Madole (NLM)) were grown in magenta boxes, and leaf discs were cut onto 15×150 mm plates. *Agrobacterium tumefaciens* containing each nucleic acid construct were collected by centrifugation of 20 ml cell suspension in 50 ml centrifuge tube at 3500 rpm for 10 minutes. Supernatant was removed and the *Agrobacterium* cell pellet was re-suspended in 40 ml liquid re-suspension medium. About 25 ml of the solution was transferred to each 15×100 mm petri plates. In those 15×150 mm plates, tobacco leaves were cut into 0.6 cm discs (avoiding the midrib).

Leaves were placed upside down, a thin layer of MS/B5 liquid re-suspension medium was added, and leaf discs were produced using a #15 razor blade. The leaf discs were poked uniformly with a fine point needle. Eight discs were placed in each regeneration plate (15×100 mm). *Agrobacterium* tumefaciens suspension was added and incubated with the leaf discs for 10 minutes. Leaf discs were transferred to co-cultivation plates (1/2MS medium) and discs were placed upside down in contact with filter paper overlaid on the co-cultivation TOM medium (MS medium with 20 g sucrose/L; 1 mg/L IAA and 2.5 mg/L BAP). The plate was sealed with parafilm and labeled appropriately.

Plates were incubated in dim light (60-80 mE/ms) under 18/6 photoperiods at 24° C. for three days. Leaf discs were transferred to regeneration/selection medium plates with TOM K media (TOM medium with 300 mg/L kanamycin) and sub-cultured bi-weekly in the same fresh medium in dim light at 24° C. until shoots become excisable. Shoots from leaves were removed with forceps and inserted in MS basal medium with 100 mg/L kanamycin for rooting at 24° C. under 18/6 photoperiods in dim light (60-80 mE/ms). When plantlets having both shoots and roots grew large enough (e.g., reached over half of the height of the GA7 box), they were transferred to soil for acclimatization. During the transfer, any gel remaining on the root tissue was washed off with tap water. Established seedlings were transferred to the greenhouse to set seed and for further analysis.

An RNAi sequence against TLA2 is provided in SEQ ID NO:27. The sense, spacer and antisense portions of the RNAi molecule are provided in SEQ ID NOs: 45-47, respectively. An RNAi sequence against TLA3 is provided in SEQ ID NO:28. The sense, spacer and antisense portions of the RNAi molecule are provided in SEQ ID NOs: 48-50, respectively. An RNAi sequence against TLA4 is provided in SEQ ID NO:29. The sense, spacer and antisense portions of the RNAi molecule are provided in SEQ ID NOs: 51-53, respectively. An RNAi sequence against CAO-2, CAO-3 and CAO-4 is provided in SEQ ID NO:30. The sense, spacer and antisense portions of the RNAi molecule are provided in SEQ ID NOs: 54-56, respectively.

Figure 2A:
FIG. 2A is a photograph of T0 tobacco plants transgenic for a RNAi nucleic acid molecule directed toward TLA3 (the three plants on the left, from left to right: TLA3i-5, TLA3i-2, and TLA3i-3) and a wild type tobacco plant (far right).
Figure 2B:
FIG. 2B is a photograph of a T1 tobacco plant transgenic for a nucleic acid molecule directed toward TLA3 (TLA3i-3).
Figure 2C:
FIG. 2C is a photograph of a T1 tobacco plant transgenic for a nucleic acid molecule directed toward TLA3 (TLA3i1-1).
Figure 3:
FIG. 3 is a photograph of a wild type tobacco plant (left) and a T0 tobacco plant transgenic for a RNAi nucleic acid molecule directed toward TLA4 (TLA4; right).

FIGS. 1, 2 and 3 shows that transgenic tobacco plants expressing a RNAi construct against a TLA gene exhibit lower chlorophyll levels depends on the target gene and integration event. As described herein, chlorophyll levels can be qualitatively determined by observing the color of the leaf and/or quantitatively determined by measuring the amount of total chlorophyll and/or the ratio of chlorophyll a to chlorophyll b.

Example 4—Real Time PCR Confirmation and Western Blot Evaluation on TLA RNAi Transgenic Lines RealTime PCR analysis: To confirm the expression pattern of selected candidate genes, relative changes in transcripts from 16 different samples were measured. In brief, total RNA was isolated using TRI Reagent (Sigma-Aldritch). To remove DNA impurities, purified RNA was treated with RNase free DNase (Turbo DNA-free; Ambion). To synthesize the first cDNA strand, approximately 10 µg of total RNA was transcribed utilizing the High Capacity cDNA Kit (Applied Biosystems). To measure the level of selected gene transcripts in the samples, RT PCR was performed using SYBR Green PCR Master Mix (Applied Biosystems). Gene specific primers are shown below.

Antigenic domains were identified from the sequences of the TLA2, TLA3 and TLA4 proteins. The oligopeptides shown in the Table below were synthesized and injected into rabbit to generate polyclonal antibodies. Western blots then were used to confirm the protein expression level for the target knock down genes.

Oligopeptides (solid underlining or dashed underlining represents different charges for the amino acids), and the ratio is the ratio of polar amino acids to total amino acids:

TLA2

NGGGKTTSLGKLANRLKKEG [SEQ ID NO: 32; corresponds to positions 178-197 of SEQ ID NO: 12] (11:20)

RGGCVVSVVDELGIPVKFVGVGE [SEQ ID NO: 33; corresponds to positions 330-352 of SEQ ID NO: 12] (7:23)

TLA3

KRGKGENVEYLVKWKDGEDN [SEQ ID NO: 34; corresponds to positions 275-294 of SEQ ID NO: 16] (13:20)

RTALLFVSGLGSEPCVKLLAEA [SEQ ID NO: 35; corresponds to positions 158-179 of SEQ ID NO: 16] (8:22)

TLA4

RRSESRKQFADSGSTRPGPR [SEQ ID NO: 36; corresponds to positions 538-557 of SEQ ID NO: 20] (14:20)

LKEVKRVLNPTEVLLVVD [SEQ ID NO: 37; corresponds to positions 279-296 of SEQ ID NO: 20] (8:18)

Figure 1B:
FIG. 1B is a photograph of a T1 tobacco plant transgenic for a RNAi nucleic acid molecule directed toward TLA2 (TLA2i-1).

FIGS. 1, 2 and 3 are photographs of the transgenic plants described herein. FIG. 1A shows a T0 transgenic tobacco plant containing a TLA2 RNAi construct (right) next to a wild type tobacco plant (left), while FIG. 1B shows a T1 transgenic tobacco plant containing a TLA2 RNAi construct. FIG. 2A shows T0 transgenic tobacco plants containing different integration events for a TLA3 RNAi construct (the three plants on the left) next to a wild type tobacco plant (the plant on the right). FIGS. 2B and 2C show two T1 transgenic tobacco plants containing a TLA3 RNAi construct. FIG. 3 shows transgenic tobacco plants containing a TLA4 RNAi construct (right) next to wild type tobacco plants (left).

TABLE 3

Real time PCR primers list

| Designation | Sequence (5' to 3') | SEQ ID NO: |
|---|---|---|
| TLA2-F1 | ATGGCTTCTCTATTATCTTCTCGTCTC | 38 |
| TLA2-R1 | GTTCAAATGCTCAGCTGGTGGAACG | 39 |
| TLA3-F1 | CGTCAATTCCTCTCTCTCCCGCCTC | 40 |
| TLA3-R1 | CTTCAGAACCAGCAGCAACAAGCAG | 41 |

TABLE 3-continued

Real time PCR primers list

| Designation | Sequence (5' to 3') | SEQ ID NO: |
|---|---|---|
| TLA4-F1 | ATGGAAGCCACTGCTTCTTTCTCCTC | 42 |
| TLA4-R1 | CTCATTCACTAGGGATACATGGAGGGTG | 43 |

Total tobacco leaf protein extracts from TLA3-RNAi transgenic plants (e.g., TLA3-1, 691 WT, and TLA3-18) were loaded (on the basis of equal Chl) and run on an SDS-PAGE gel. Western blotting was performed on the SDS-PAGE gel and the membrane was probed with specific polyclonal antibodies raised against two TLA3 oligopeptides (primary anti-TLA3 antibody diluted at 1:500). Substantially lower amounts of the TLA3 protein was observed in the extracts from the TLA3-1 and TLA3-18 plants compared to that of the wild type plants.

Interestingly, the TLA3 protein from *N. tabacum* has a predicted molecular weight of 35 kD, but, under electrophoretic conditions, the protein migrates to a position of about 25 kD. This faster electrophoretic mobility is attributed to the fact that TLA3 from *N. tabacum* has about 45 negatively charged amino acids and, thus, migrates faster under the influence of the electrophoresis field.

Figure 4A:
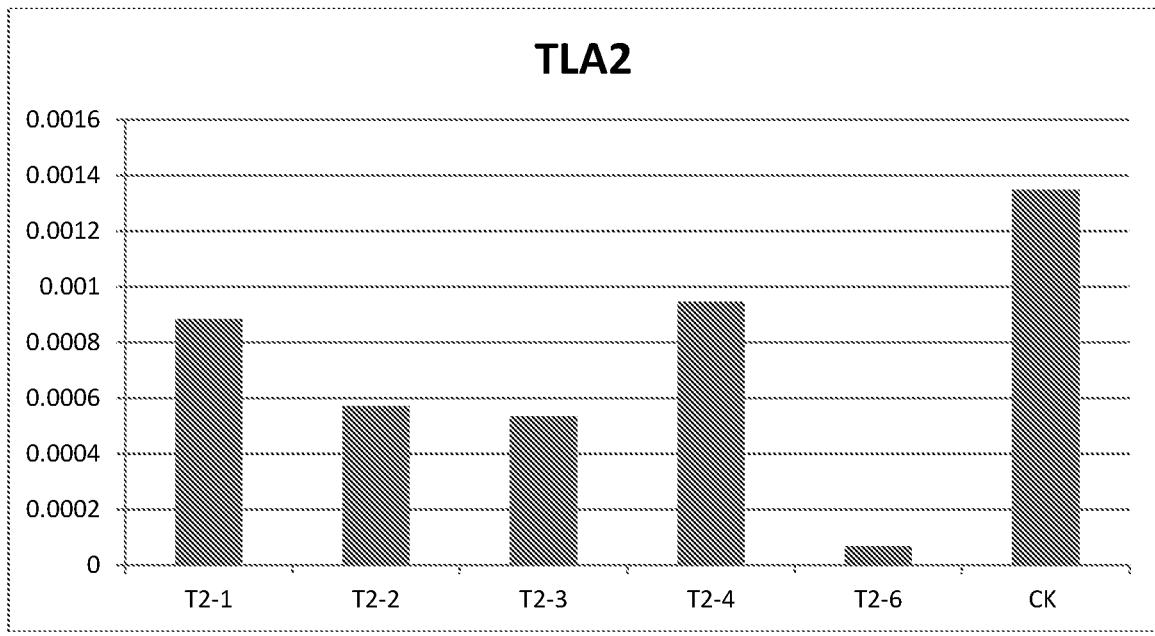
FIG. 4A is a graph showing the amount of TLA2 mRNA in T0 tobacco plants transgenic for RNAi nucleic acid molecules directed toward TLA2.

FIG. 4A is a graph showing the real time PCR results from T0 generation plants transgenic for TLA2 RNAi. The T2-1, T2-2, T2-3, T2-4 and T2-6 designations represent individual TLA2 RNAi transgenic plants while CK refers to a transgenic control tobacco plant (transformed with an empty vector). The Y axis ($2\bigcirc-\Delta Ct$) shows the relative expression level, based on mRNA levels, of the TLA2 gene. There were different levels of knock-down of the TLA2 gene depending upon the particular integration event. Among them, the T2-6 line exhibited plants with stunted growth; most of the plants died before they matured. Overall, regenerating transgenic tobacco plants deficient in TAL2 was difficult, and the growth was inhibited by the level of TLA2 knock-down.

Figure 4B:
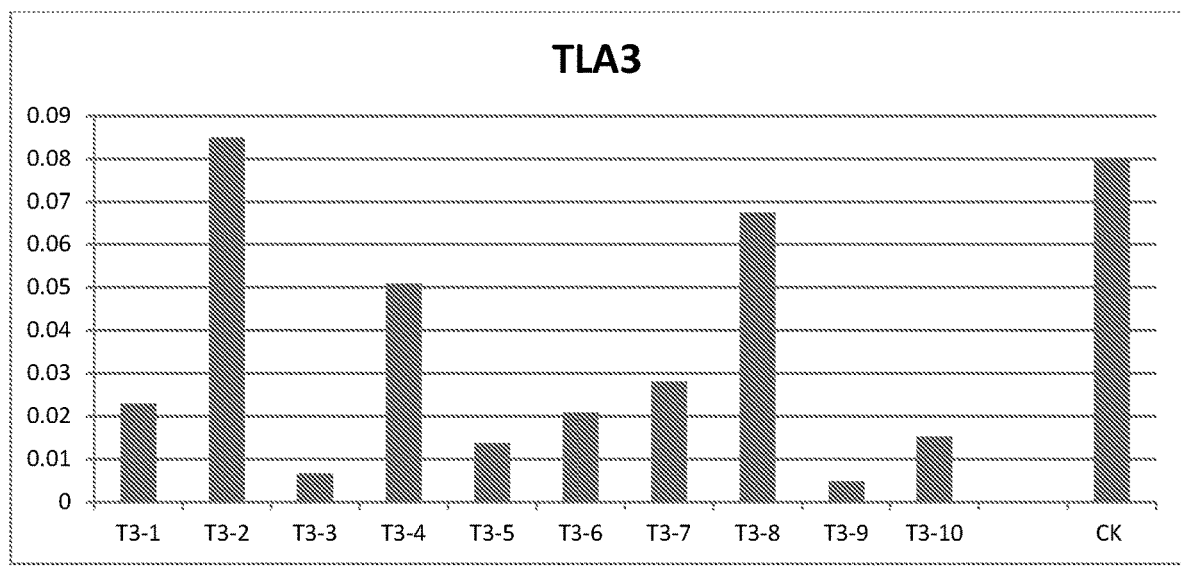
FIG. 4B is a graph showing the amount of TLA3 mRNA in T0 tobacco plants transgenic for RNAi nucleic acid molecules directed toward TLA3.

FIG. 4B is a graph showing the real time PCR results in T0 generation plants transgenic for TLA3 RNAi. T3-1 to T3-10 designations represent individual TLA3 RNAi transgenic plants, whereas CK refers to transgenic control tobacco (e.g., transformed with an empty vector). As with TLA2 transformants, there were different levels of knock down of TLA3 gene in TLA3 RNAi transformants.

Example 5—Phenotype Evaluation on TLA RNAi Transgenic Lines

According to the TLA concept proposed by the University of California—Berkeley group (Polle et al., 2003, Planta, 217:49-59; Kirst et al., 2012, Plant Physiol., 158:930-45; and Kirst et al., 2012, Plant Physiol., 160:2251-60), the mutants described herein should result in smaller light-harvesting chlorophyll antenna size and a substantially improved photosynthetic efficiency, as well as a higher [chlorophyll a/chlorophyll b] ratio. The chlorophyll from tobacco leaf samples was extracted in 80% acetone, and cell debris was removed by centrifugation at 20,000×g for 5 min. The absorbance of the supernatant was measured with a Shimadzu UV-1800 spectrophotometer, and the Chl concentration of the samples was determined according to Arnon (1949, Plant Physiol., 24:1-15), with equations corrected as described by Melis et al. (1989, Philos. Trans. R. Soc. Lond. B, 323:397-409). Total carotenoid content was determined according to the method of Lichtenthaler (1987, Methods Enzymol., 148:350-82).

The antenna size of tobacco leaf samples was calculated by measuring photosynthetic activity. The oxygen evolution activity of the tobacco leaf (punched from fresh leaf tissue sample) was measured at 25° C. with a Clark-type oxygen electrode illuminated with light from a halogen lamp projector. A Corning 3-69 filter (510-nm cutoff filter) defined the yellow actinic excitation via which photosynthesis measurements were made. Samples of 5-mL cell suspension containing 1.3 mM Chl were loaded into the oxygen electrode chamber. Sodium bicarbonate (100 mL of 0.5 M solution, pH 7.4) was added to the cell suspension prior to the oxygen evolution measurements to ensure that oxygen evolution was not limited by the carbon supply available to the cells. After registration of the rate of dark respiration by the cells, samples were illuminated with gradually increasing light intensities. The rate of oxygen exchange (uptake or evolution) under each of these irradiance conditions was recorded continuously for a period of about 5 min.

The following Table shows total chlorophyll measurement and Chlorophyll a/Chlorophyll b ratios of T0 lines transgenic for TLA2, TLA3 or TLA4 RNAi.

TABLE 4

Chlorophyll measurements

| Sample | Chl a (µg/mL) | Chl b (µg/mL) | total Chl (µg/mL) | Chl a/b Ratio |
|---|---|---|---|---|
| BW1* | 17.96 | 4.29 | 22.240 | 4.190 |
| BM2* | 5.56 | 0.61 | 6.165 | 9.190 |
| Wild type | 43.07 | 11.40 | 54.465 | 3.780 |
| TLA2-1 | 29.90 | 5.97 | 35.860 | 5.012 |
| TLA2-2 | 26.40 | 6.56 | 32.950 | 4.027 |
| TLA2-3 | 5.93 | 1.29 | 7.215 | 4.615 |
| TLA2-4 | 20.34 | 4.68 | 25.015 | 4.351 |
| TLA2-5 | 50.73 | 13.85 | 64.570 | 3.664 |
| TLA2-6 | 18.78 | 4.76 | 23.535 | 3.944 |
| TLA2-7 | 24.09 | 5.55 | 29.640 | 4.341 |
| TLA3-1 | 29.53 | 6.66 | 36.185 | 4.433 |
| TLA3-2 | 45.05 | 11.00 | 56.040 | 4.097 |
| TLA3-3 | 43.16 | 6.10 | 49.255 | 7.081 |
| TLA3-4 | 36.73 | 9.04 | 45.770 | 4.063 |
| TLA3-5 | 38.05 | 7.22 | 45.265 | 5.274 |
| TLA3-6 | 27.72 | 5.01 | 32.720 | 5.537 |
| TLA3-7 | 30.27 | 5.27 | 35.540 | 5.744 |
| TLA3-8 | 53.82 | 13.29 | 67.105 | 4.049 |
| TLA3-9 | 29.61 | 4.95 | 34.555 | 5.988 |
| TLA3-10 | 24.09 | 4.45 | 28.535 | 5.420 |
| TLA3-11 | 36.04 | 5.31 | 41.340 | 6.793 |
| TLA3-12 | 28.50 | 4.27 | 32.770 | 6.674 |
| TLA3-13 | 33.61 | 5.63 | 39.235 | 5.969 |
| TLA3-14 | 22.65 | 3.75 | 26.400 | 6.040 |
| TLA3-15 | 21.62 | 3.29 | 24.910 | 6.571 |
| TLA3-16 | 27.80 | 5.77 | 33.565 | 4.817 |
| TLA3-17 | 33.03 | 6.90 | 39.920 | 4.790 |
| TLA3-18 | 27.34 | 7.35 | 34.690 | 3.720 |
| TLA3-19 | 30.06 | 6.67 | 36.725 | 4.510 |
| TLA3-20 | 23.56 | 4.44 | 27.995 | 5.305 |
| TLA3-21 | 21.25 | 2.89 | 24.135 | 7.366 |

TABLE 4-continued

Chlorophyll measurements

| Sample | Chl a (µg/mL) | Chl b (µg/mL) | total Chl (µg/mL) | Chl a/b Ratio |
|---|---|---|---|---|
| TLA3-22 | 22.28 | 4.17 | 26.450 | 5.343 |
| TLA4-1 | 8.90 | 2.07 | 10.960 | 4.308 |
| TLA4-2 | 46.74 | 12.06 | 58.790 | 3.877 |
| TLA4-3 | 29.90 | 5.97 | 35.860 | 5.012 |
| TLA4-4 | 21.04 | 4.83 | 25.870 | 4.356 |
| TLA4-5 | 39.16 | 8.72 | 47.875 | 4.493 |
| TLA4-6 | 38.63 | 7.88 | 46.505 | 4.902 |

*BW1: UC Berkley wild type line; BM2: UC Berkley TLA mutant line

Tobacco lines exhibit a particular ratio of chlorophyll a/b, which can be used as an index for total antenna size. Therefore, changes in the chlorophyll a/b ration can be used to measure changes in antenna size. As shown in the Table above, the UC Berkeley mutant line increased the chlorophyll a/b ratio to about 9, from a wild type ratio of about 4. In the NLM tobacco lines described herein, the wild type ratio of chlorophyll a/b is about 4, but in T0 generations of NLM plants transgenic for a TLA3 RNAi, most of the mutant lines reached a chlorophyll a/b ratio of about 5 to about 8. There was no obvious increase in chlorophyll a/b ratio in the T0 generation of plants transgenic for TLA2 RNAi and TLA4 RNAi. These results indicate that TLA3 likely is the initial candidate gene to knock down and decrease antenna size in photosynthetic light harvesting centers in tobacco.

T1 generation of TLA3 RNAi line 1 (501-1 to 501-24) and 3 (data not shown) were harvested and chlorophyll a/b ratios were determined. The following Table shows chlorophyll data for the T1 generation of the TLA3 RNAi plants. The chlorophyll a/b ratios in the T1 generation of the TLA3 RNAi plants were higher compared to wild type ratios, and the change in the ratio was stable in the T1 generation.

TABLE 5

Chlorophyll measurements

| Sample | Chl a (µg/mL) | Chl b (µg/mL) | total Chl (µg/mL) | Chl a/b Ratio |
|---|---|---|---|---|
| 503_1 | 19.48 | 2.58 | 22.06 | 7.57 |
| 503_2 | 31.14 | 6.85 | 37.99 | 4.55 |
| 503_3 | 32.94 | 7.37 | 40.32 | 4.47 |
| 503_4 | 31.71 | 6.59 | 38.30 | 4.81 |
| 503_5 | 44.48 | 8.26 | 52.74 | 5.38 |
| 503_6 | 44.88 | 9.67 | 54.56 | 4.64 |
| 503_7 | 49.16 | 10.74 | 59.89 | 4.58 |
| 503_8 | 38.81 | 8.09 | 46.90 | 4.80 |
| 503_9 | 40.97 | 9.89 | 50.86 | 4.14 |
| 503_10 | 33.30 | 7.27 | 40.57 | 4.58 |
| 503_11 | 29.03 | 5.86 | 34.89 | 4.95 |
| 503_12 | 33.10 | 7.77 | 40.87 | 4.26 |
| 503_13 | 30.27 | 5.62 | 35.88 | 5.39 |
| 503_14 | 34.49 | 6.89 | 41.38 | 5.01 |
| 503_15 | 36.55 | 7.74 | 44.28 | 4.72 |
| 503_16 | 34.80 | 7.00 | 41.79 | 4.97 |
| 503_17 | 42.21 | 8.61 | 50.81 | 4.90 |
| 503_18 | 20.70 | 3.24 | 23.93 | 6.39 |
| 503_19 | 38.04 | 8.50 | 46.54 | 4.48 |
| 503_20 | 38.30 | 7.79 | 46.08 | 4.92 |
| 503_21 | 29.45 | 4.86 | 34.31 | 6.06 |
| 503_22 | 34.28 | 8.08 | 42.36 | 4.24 |
| 503_23 | 29.14 | 5.79 | 34.92 | 5.04 |
| 503_24 | 28.36 | 8.96 | 37.31 | 3.17 |
| Wild type | 46.61 | 13.67 | 60.27 | 3.41 |

Antenna size of the photosynthetic light harvesting centers (both PSI and PSII) were measured in the T1 generation for TLA3 RNAi plants, TLA2 RNAi plants, and TLA4 RNAi plants. The following Table shows the antenna size measurement of PSI and PSII in the T1 generation for four TLA2 RNAi line 2 plants (e.g., 2-1-1, 2-1-2, 2-1-3, and 2-1-4). The data showed that total antenna size in PSI for mutant lines was similar to wild type, but that PSII antenna size decreased in TLA2 knock out lines.

TABLE 6

Chlorophyll and antenna measurements

| Sample number | Chl a content (µg/ml) | Chl b content (µg/ml) | Total Chl (µg/ml) | Total Car (µg/ml) | Chl a/b ratio (mol:mol) | Chl/Car ratio (mol:mol) | PSII antenna size (molecules in PSII) | PSI antenna size (molecule in PSI) |
|---|---|---|---|---|---|---|---|---|
| WT 1 | 18.84 | 5.93 | 24.77 | 5.48 | 3.18 (2.70*) | 4.52 (5.54*) | 215 | 180 |
| WT 2 | 25.37 | 7.94 | 33.30 | 6.64 | 3.20 (2.73*) | 5.02 (5.98*) | 185 | 197 |
| 2-1-1 | 18.13 | 5.29 | 23.42 | 4.93 | 3.43 (3.02*) | 4.75 (6.16*) | 164 | 178 |
| 2-1-2 | 11.59 | 3.81 | 15.40 | 2.57 | 3.04 (2.88*) | 6.00 (6.56*) | 125 | 168 |
| 2-1-3 | 17.90 | 4.73 | 22.63 | 4.48 | 3.79 (3.02*) | 5.05 (6.66*) | 125 | 184 |
| 2-1-4 | 12.23 | 4.26 | 16.48 | 2.76 | 2.87 (2.92*) | 5.98 (6.24*) | 125 | 166 |

*ratios measured in isolated thylakoids

The antenna size for PSI and PSII in the T1 generation of TLA3 RNAi line 3 plants (e.g., 3-3-1, 3-3-2, 3-3-3, 3-3-4, 3-3-5, 3-3-6, and 3-3-7) is shown in the following Table. Notably, the total number of photoreceptor antenna was knocked down in the transgenic plants from 215 to 160 for PSII and from 195 to 160 for PSI. The decrease in antenna size was correlated with the increase in chlorophyll a/b ratio in the T1 generation.

TABLE 7

Chlorophyll and antenna measurements

| Sample | Chl a [µg/ml] | Chl b [µg/ml] | Tot Chl* [µg/ml] | Total Car [µg/ml] | Chl a/b (mol:mol) | Chl/Car (mol:mol) | PSII antenna size (molecules in PSII) | PSI antenna size (molecules in PSII) |
|---|---|---|---|---|---|---|---|---|
| WT 1 | 32.1 | 11 | 43.1 | 7.91 | 2.91 | 5.46 | 215 | 195 |
| WT 2 | 26.6 | 8.83 | 35.5 | 6.29 | 3.02 | 5.64 | | |
| 3-3-1 | 16.8 | 3.68 | 20.5 | 4.4 | 4.56 | 4.65 | 160 | 164 |
| 3-3-2 | 15.1 | 3.43 | 18.5 | 4.12 | 4.4 | 4.49 | | |
| 3-3-3 | 13.9 | 3.26 | 17.1 | 3.4 | 4.26 | 5.04 | | |
| 3-3-4 | 14.6 | 3.36 | 18 | 3.57 | 4.34 | 5.03 | | |
| 3-3-5 | 15.8 | 3.54 | 19.4 | 4.66 | 4.47 | 4.16 | 148 | 162 |
| 3-3-6 | 32.1 | 11 | 43.1 | 7.91 | 2.91 | 5.46 | 215 | 195 |
| 3-3-7 | 26.6 | 8.83 | 35.5 | 6.29 | 3.02 | 5.64 | | |

The following Table shows antenna size in PSI and PSII from T1 generation plants transgenic for TLA4 RNAi line 2 and line 6. This data demonstrated that total antenna size of the mutant lines was similar to that of the wild type in both PSI and PSII.

TABLE 8

Chlorophyll and antenna measurements

| Sample | Chl a | Chl b | Tot Chl* | Total Car | Chl a/b | Chl/Car | PSII antenna size | PSI antenna size |
|---|---|---|---|---|---|---|---|---|
| WT 1 | 24.1 | 8.0 | 32.0 | 5.40 | 3.00 | 5.86 | 210 | |
| WT 2 | 27.3 | 9.2 | 36.5 | 6.29 | 2.93 | 6.03 | 200 | 195 |
| TLA4-2-1 | 30.1 | 10.8 | 41.0 | 6.30 | 2.76 | 6.48 | | |
| TLA4-2-2 | 32.9 | 12.0 | 45.0 | 6.80 | 2.72 | 6.55 | 232 | |
| TLA4-2-4 | 29.3 | 11.1 | 40.5 | 6.10 | 2.63 | 6.59 | 190 | |
| TLA4-6-1 | 29.3 | 11.1 | 40.5 | 6.10 | 2.63 | 6.59 | 156 | 165 |
| TLA4-6-2 | 27.9 | 9.7 | 37.7 | 6.30 | 2.85 | 5.90 | 230 | |
| TLA4-6-3 | 25.7 | 10.2 | 36.0 | 5.40 | 2.52 | 6.64 | 185 | 145 |

Example 6—CAO RNAi Plant Generation

Tobacco plants transgenic for the CAO RNAi nucleic acid shown in SEQ ID NO:30 were produced as described herein, and chlorophyll a and chlorophyll b was measured as described herein. The data is shown in the following Table.

TABLE 9

Chlorophyll measurements

| Sample | Chl A (µg/mL) | Chl B (µg/mL) | Total (µg/mL) | Chl a/b Ratio |
|---|---|---|---|---|
| Wild type | 17.56 | 4.42 | 21.97 | 3.97 |
| CAOi-1 | 15.75 | 2.49 | 18.23 | 6.33 |
| CAOi-2 | 12.73 | 1.78 | 14.50 | 7.16 |

Figure 5A:
FIG. 5A is a photograph of a T0 generation tobacco plant transgenic for CAOi-1.
Figure 5B:
FIG. 5B is a photograph of a T0 generation tobacco plant transgenic for CAOi-2.

This data demonstrated that antenna size of the mutant lines was decreased relative to that of the wild type plants. FIG. 5A shows a T0 generation tobacco plant transgenic for CAOi-1, and FIG. 5B shows a T0 generation tobacco plant transgenic for CAOi-2.

Example 7—Phenotypes of TLA3 RNAi Plants

Decreasing, or truncating, the chlorophyll antenna size of the photosystems should improve photosynthetic solar energy conversion efficiency and productivity in mass cultures of algae or plants by up to 3-fold. A Truncated Light-harvesting chlorophyll Antenna size (TLA) in photosynthetic organisms should help alleviate excess absorption of sunlight and the ensuing wasteful non-photochemical dissipation of excitation energy and, thus, would increase solar-to-biomass energy conversion efficiency and photosynthetic productivity in high density cultures.

Tobacco was grown under conditions that result in high-density canopies to evaluate the TLA plants described herein. The T0 stage of multiple NL Madole TLA3-RNAi transformants were screened and selected to identify lines for generating T1 seeds. The latter were germinated and T1 leaves were subjected to phenotypic and functional analysis. Plants were grown in high density canopies, with the canopy layout of 25 plants in a 5×5 configuration, and the distance between individual plants set at 9 inches. Biochemical analysis and biomass accumulation was performed.

This work showed a 25% improvement in stem and leaf biomass accumulation for the TLA tobacco canopies over that of their wild-type counterparts grown under the same ambient conditions. Distinct differences were observed in the appearance of the canopy between plants containing a TLA RNAi and wild type tobacco plants. For example, the TLA3-RNAi canopy was a light-green color, while the wild type canopy was a much darker green. The results described herein can lead to significant improvements in agronomy, agricultural productivity, and the optimization of photosynthesis in commodity crops (e.g., tobacco) or parts thereof (e.g., leaves).

The average biomass values were determined for four different canopies. The results demonstrated that canopy interior plants performed better than plants in the periphery, as would be expected from the greater transmittance of sunlight. Significantly, an increase in leaf biomass of 10.2% was observed for the canopy interior TLA3-RNAi plants as compared to that of the corresponding wild type plants.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of making a *Nicotiana tabacum* plant, comprising:
   selecting a *N. tabacum* plant comprising a non-natural mutation in an endogenous nucleic acid sequence selected from the group consisting of SEQ ID NOs: 21, 23, and 25;
   crossing or selfing said selected *N. tabacum* plant to produce at least one progeny seed; and
   obtaining at least one progeny *N. tabacum* plant grown from said at least one progeny seed, wherein said at least one progeny *N. tabacum* plant comprises said non-natural mutation; and
   wherein said at least one progeny *N. tabacum* plant comprising said non-natural mutation has reduced expression of a nucleic acid sequence selected from the group consisting of SEQ ID NOs: 21, 23, and 25 compared to a control tobacco plant lacking said non-natural mutation.

2. The method of claim 1, further comprising:
   curing tobacco leaves from said at least one progeny *N. tabacum* plant to produce cured tobacco leaves; and
   producing a tobacco product from said cured tobacco leaves.

3. The method of claim 2, wherein said tobacco product is selected from the group consisting of cigarettes, smokeless tobacco products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

4. The method of claim 1, wherein said endogenous nucleic acid sequence encodes a polypeptide selected from the group consisting of SEQ ID NOs:22, 24, and 26.

5. The method of claim 1, wherein said at least one progeny *N. tabacum* plant comprises a reduced amount of mRNA corresponding to SEQ ID NO:21, 23, or 25, a reduced amount of polypeptide comprising SEQ ID NO: 22, 24, or 26, reduced activity of a polypeptide selected from the group consisting of SEQ ID NOs: 22, 24, or 26; or a combination thereof.

6. The method of claim 1, wherein said at least one progeny *N. tabacum* plant comprises a reduced concentration of thylakoid membranes in the photosystems; a reduced amount of total chlorophyll; an increased ratio of chlorophyll a to chlorophyll b; or a combination thereof; wherein said reduced or increased amounts or ratio are relative to a *N. tabacum* plant lacking said non-natural mutation.

7. The method of claim 1, wherein leaf from the at least one progeny *N. tabacum* plant exhibits comparable or better quality than leaf from a *N. tabacum* plant lacking said non-natural mutation.

8. The method of claim 1, wherein said *N. tabacum* plant is a Burley type, a dark type, a flue-cured type, or an Oriental type.

9. A *N. tabacum* plant, or part thereof, comprising an altered photosynthesis phenotype and reduced activity of a polypeptide selected from the group consisting of SEQ ID NOs: 22, 24, and 26; wherein said altered photosynthesis phenotype is selected from the group consisting of a reduced concentration of thylakoid membranes in the photosystems, a reduced amount of total chlorophyll, and an increased ratio of chlorophyll a to chlorophyll b; wherein said reduced or increased amounts or ratio are in comparison to a *N. tabacum* plant having wild-type activity of a polypeptide selected from the group consisting of SEQ ID NOs: 22, 24, and 26.

10. The *N. tabacum* plant, or part thereof, of claim 9, wherein said reduced activity comprises a reduced amount of a polypeptide selected from the group consisting of SEQ ID NOs: 22, 24, and 26 compared to a *N. tabacum* plant having a wild-type amount of said polypeptide.

11. The *N. tabacum* plant, or part thereof, of claim 9, wherein leaf from said *N. tabacum* plant, or part thereof, exhibits comparable or better quality than leaf from a control *N. tabacum* plant lacking said mutation.

12. Cured leaf from the *N. tabacum* plant of claim 9.

13. A tobacco product comprising the cured leaf of claim 12.

14. The tobacco product of claim 13, wherein said tobacco product is selected from the group consisting of cigarettes, smokeless tobacco products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

15. A *N. tabacum* plant, or part thereof, comprising a non-natural mutation in an endogenous nucleic acid, the wild type endogenous nucleic acid encoding a sequence selected from the group consisting of -SEQ ID NOs: 22, 24, and 26; wherein said *N. tabacum* plant comprising said non-natural mutation has reduced expression of a nucleic acid sequence selected from the group consisting of SEQ ID NOs: 21, 23, and 25 compared to a control tobacco plant lacking said non-natural mutation.

16. The *N. tabacum* plant, or part thereof, of claim 15, wherein leaf from said *N. tabacum* plant comprises a reduced amount of mRNA corresponding to a sequence selected from the group consisting of SEQ ID NOs:21, 23, and 25; a reduced amount of a polypeptide selected from the group consisting of SEQ ID NOs: 22, 24, and 26; reduced activity of a polypeptide selected from the group consisting of SEQ ID NOs: 22, 24, and 26; or a combination thereof.

17. The *N. tabacum* plant, or part thereof, of claim 15, wherein leaf from said *N. tabacum* plant exhibits comparable or better quality compared to leaf from a plant lacking said non-natural mutation.

18. Cured leaf from the *N. tabacum* plant of claim 15.

19. A tobacco product comprising the cured leaf of claim 18.

20. The tobacco product of claim 19, wherein said tobacco product is selected from the group consisting of cigarettes, smokeless tobacco products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

* * * * *